(12) United States Patent
Bollag et al.

(10) Patent No.: US 6,326,397 B1
(45) Date of Patent: Dec. 4, 2001

(54) RETINOID ANTAGONISTS AND USE THEREOF

(75) Inventors: Werner Bollag, Basel (CH); Michael Klaus, Weil am Rhein (DE); Peter Mohr, Basel (CH); Paola Panina-Bordignon, Milan (IT); Michael Rosenberger, Caldwell, NJ (US); Francesco Sinigaglia, Milan (IT)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/307,009

(22) Filed: May 7, 1999

Related U.S. Application Data

(63) Continuation-in-part of application No. 09/189,189, filed on Nov. 10, 1998.

(51) Int. Cl.[7] ........................... A01N 53/00; C07C 59/00; C07C 9/76

(52) U.S. Cl. ............... 514/531; 560/55; 560/59; 562/465; 562/469; 554/218; 568/442; 514/502; 514/570

(58) Field of Search ........................... 560/100, 104, 560/106, 112, 113, 55, 59; 562/490, 495, 465, 469; 564/180, 182; 568/308, 328, 425, 444, 442; 554/218; 514/531, 532, 570

(56) References Cited

U.S. PATENT DOCUMENTS

| | | |
|---|---|---|
| 5,391,766 | 2/1995 | Klaus et al. . |
| 5,512,683 | 4/1996 | Klaus et al. . |
| 5,705,167 | 1/1998 | Bernardon et al. . |
| 5,801,253 | 9/1998 | Klaus et al. . |
| 5,986,131 | 11/1999 | Klaus et al. . |
| 6,030,964 | * 2/2000 | Hibi et al. . |

FOREIGN PATENT DOCUMENTS

| | | |
|---|---|---|
| 728 742 | 8/1996 | (EP) . |
| WO 96 05165 | 2/1996 | (WO) . |
| 96/20913 | 7/1996 | (WO) . |
| WO 96/20913 | * 7/1996 | (WO) . |
| 97/09297 | 3/1997 | (WO) . |

OTHER PUBLICATIONS

M. Dawson W. Okamura "Chem. & Biol. of Synthetic Retinoids." CRC Press: 1990.*
Klein et al., The Journal of Biological Chemistry, 271:22692–22696 (1996).
Teng et al., J. Med. Chem., 40:2445–2451 (1997).
Kaneko et al., Med. Chem. Res., 1:220–225 (1991).
Kagechika et al., Biochem. & Biophys. Res. Comm., 231:243–248 (1997).
Eyrolles et al., J. Med. Chem., 37:1508–1517 (1994).
Charpentier et al., J. Med. Chem., 38:4993–5006 (1995).
Dawson et al., Cancer Research, 55:4446–4451 (1995).
Yoshimura et al., J. Med. Chem., 38:3163–3173 (1995).
Lee et al., The Journal of Biological Chemistry, 271:11897–11903 (1996).
Koch et al., J. Med. Chem., 39:3229–3234 (1996).
Lala et al., Letter to Nature, 383:450–453 (1996).
Romagnani, Annu. Rev. Immunol., 12, 227–257 (1994).
Robinson et al, Chem. Immunol., 63:187–203 (1996).
Abbas et al., Nature, 383:787–793 (1996).
Gavett et al., J. Exp. Med., 182;1527–1536 (1995).
Johnson et al., J. Med. Chem., 38:4764–4767 (1995).
Klein et la., J. Biol. Chem., 271:22692–22696 (1996).
Kips et al., Am. J. Respir. Crit. Care Med., 153:535–539 (1996).
Apfel et al, Proc. Natl. Acad. Sci., 89, pp 7129–7133 (1992).

* cited by examiner

*Primary Examiner*—Paul J. Killos
(74) *Attorney, Agent, or Firm*—George W. Johnston; John P. Parise

(57) ABSTRACT

The present invention relates to novel retinoid antagonists of the formula I

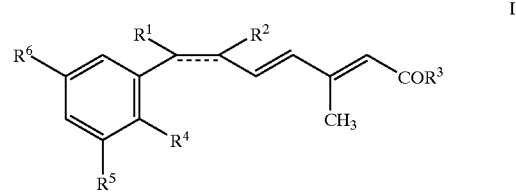

wherein the dotted bond can be either hydrogenated or form a double bond; and, when the dotted bond forms a double bond, $R^1$ is lower alkyl and $R^2$ is hydrogen; and, when the dotted bond is hydrogenated, $R^1$ and $R^2$ taken together are methylene to form a cis-substituted cyclopropyl ring; $R^3$ is hydroxy or lower alkoxy; $R^4$ is alkyl or alkoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule to form a quaternary carbon atom pharmaceutically acceptable salts of carbocylic acids of the formula I; as well as method for the treatment of osteoporosis and preneoplastic and neoplastic diseases, and a method for reducing or abolishing adverse events in subjects receiving retinoid agonist treatment by administering a retinoid antagonist.

16 Claims, 5 Drawing Sheets

RETINOID ANTAGONISTS AND USE THEREOF

This is a continuation-in-part of U.S. Ser. No. 09/189,189, filed Nov. 10, 1998.

BACKGROUND OF THE INVENTION

Retinoids are a class of compounds structurally related to vitamin A, comprising natural and synthetic compounds. Retinoids have been found to be clinically useful in the treatment of dermatological and oncological diseases.

Retinoids with retinoid receptor agonistic activity have been shown to be active not only in model systems for the treatment of dermatological and oncological diseases but also in models for the treatment of T-helper cell type 1 (Th1)-mediated immune diseases. Retinoids with retinoid receptor agonistic activity are active in the treatment of adjuvant arthritis [Brinckerhoffet al., Science 221, 756–758 (1983)] and experimental allergic encephalomyelitis [Massacesi et al., J. Clin. Invest. 88, 1331–1337 (1991); Racke et al., J. Immunol. 154, 450–458 (1995)], animal models for rheumatoid arthritis and multiple sclerosis, respectively. Both diseases are considered to belong to Th1-mediated, immune diseases.

Experimentally, retinoids with retinoid receptor antagonistic activity (retinoid antagonists) are effective in counteracting many properties of retinoids with retinoid receptor agonistic activity (retinoid agonists) such as inhibition of cell proliferation, induction of cell differentiation, induction of apoptosis and inhibition of angiogenesis [Bollag et al., Int. J. Cancer 70, 470–472 (1997)]. Retinoid antagonists are also suppressing toxic side effects of retinoid agonists such as the signs and symptoms of the hypervitaminosis A syndrome and teratogenesis [Standeven et al., Toxicol. Appl. Pharmacol. 138, 169–175 (1996); Eckhardt and Schmitt, Toxicol. Letters 70, 299–308 (1994)]. Therefore, they may be useful clinically in preventing or treating adverse events caused by retinoid agonists.

Retinoid antagonists have been proposed for clinical use in prevention and therapy of retinoid-induced toxicity and side effects, particularly of the so-called hypervitaminosis A syndrome. Retinoid antagonists have also been proposed to be used in combination with retinoid receptor agonists or other nuclear receptor agonists for prevention and treatment of preneoplastic or neoplastic lesions, vitreo-retinopathy and retinal detachment. In addition, retinoid antagonists have been proposed for use as single agents, based on their anti-proliferative effect, for treatment of certain neoplasms insensitive to retinoid receptor agonists [WO 97/09297].

SUMMARY OF THE INVENTION

The present invention relates to the compounds of the formula I

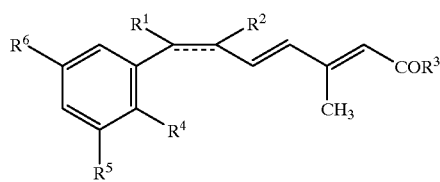

wherein the dotted bond can be either hydrogenated or form a double bond; and, when the dotted bond forms a double bond, $R^1$ is lower alkyl and $R^2$ is hydrogen; and, when the dotted bond is hydrogenated, $R^1$ and $R^2$ taken together are methylene to form a cis-substituted cyclopropyl ring; $R^3$ is hydroxy or lower alkoxy; $R^4$ is alkyl or alkoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule to form a quaternary carbon atom and pharmaceutically acceptable salts of carboxylic acids of formula I are effective in inducing IL-12 production and suppressing T-helper cell type 2 (Th2) activity and therefore are useful in treating diseases mediated by Th2 activity and Th2-related cytokines such as IL-4 and IL-5.

DETAILED DESCRIPTION OF THE INVENTION

The compounds of formula I are effective in inducing IL-12 production and suppressing T-helper cell type 2 activity as shown by the fact that all of these compounds are active in the in vitro assay of Example 4 and 5 hereinafter. Therefore, the compounds of formula I can be used to increase the production of IL-12 and to suppress T helper cell type 2 activity and are therefore useful for the treatment of T-helper cell type 2 (Th2)-mediated immune diseases.

As used herein the term "alkyl" means straight-chain, branched or cyclic alkyl residues, in particular those containing from 1 to 12 carbon atoms, such as methyl, ethyl, propyl, isopropyl, t-butyl, decyl, dodecyl, cyclopentyl, cyclohexyl, cycloheptyl and the like. The term "lower alkyl" means alkyl groups containing from 1 to 7, preferably 1–4 carbon atoms. Most preferred lower alkyl groups are methyl and ethyl. Alkyl and alkoxy groups denoted by $R^4$ preferably contain 1–8 carbon atoms, more preferably 1–4 carbon atoms. Particularly preferred group $R^4$ are ethoxy and butoxy. Examples of $C_{4-12}$ alkyl groups represented by $R^5$ or $R^6$ are tert.-butyl, 1,1-dimethylpropyl, 1-methyl-1-ethylpropyl, 1-methyl-1-ethylhexyl and 1,1-dimethyldecyl. Of these groups, tert.-butyl is preferred. When one of $R^5$ and $R^6$ is a 5 to 12 cycloalkyl hydrocarbon substituted, the substituent contains from 1 to 3 fused hydrocarbon rings which may be unsubstituted or substituted with from 1 to 3 lower alkyl groups. The substituents R5 and $R^6$ are attached to the remainder of the molecule of formula I by a carbon atom which, when so attached, forms a quaternary carbon atom. Among the preferred mono- or polycyclic hydrocarbon substituents represented by $R^5$ and $R^6$ are 1-adamantyl and. 1-methylcyclohexyl.

The compounds of formula I wherein $R^3$ is hydroxy form salts with pharmaceutically acceptable bases such as alkali salts, e.g. Na and K-salts, and ammonium or substituted ammonium salts such trimethylammonium salts which are within the scope of this invention.

In one embodiment, the invention comprises compounds of the formula I a

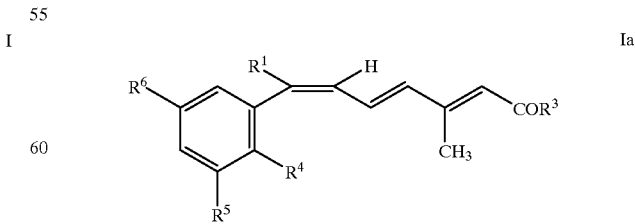

wherein $R^1$ is lower alkyl and $R^3$ to $R^6$ are as in formula I; and pharmaceutically acceptable salts of carboxylic acids of formula Ia.

In another embodiment the invention comprises compounds of the formula:

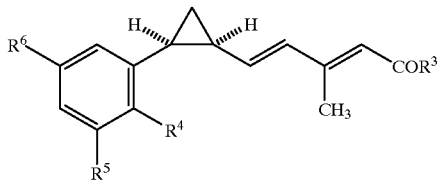

wherein $R^3$ to $R^6$ are as in formula I; and pharmaceutically acceptable salts of carboxylic acids of formula Ib.

The compounds of formula I wherein $R^1$ and $R^2$ taken together are methylene, may be present in pure enantiomeric form or as racemates. While formula Ib arbitrarily depicts a particular enantiomeric form it is to be understood that the invention also comprises the opposite enantiomers as well as the racemates.

Particularly preferred are compounds of the formula Ia wherein $R^1$ is methyl, $R^4$ is ethoxy or butoxy and $R^5$ and $R^6$ are tert.-butyl.

The compounds of formula I above bind specifically to Retinoid X Receptors (RXR), but do not activate them. Accordingly the compounds of this invention can be used to reduce or abolish adverse events induced by retinoids (retinoid agonists) in patients with dermatological or oncological diseases. Experimental investigations on this subject are described in Examples; 1–3.

In a second aspect, the present invention relates to the use of retinoid antagonists comprising retinoids with selective Retinoic Acid Receptor (RAR) antagonistic activity, Retinoid X Receptor (RXR) antagonistic activity or mixed RAR-RXR antagonistic activity, for the manufacture of a medicament for the treatment of T-helper cell type 2 (Th2)-mediated immupe diseases such as immunoglobulin E (IgE)-mediated allergic diseases, or diseases mediated by the Th2-related cytokines, as well as to the use of said active substances for the treatment of such diseases.

In accordance with that aspect of the invention the term "retinoid antagonists" is used for retinoids or compounds with RAR, RXR or mixed RAR-RXR antagonistic activity. It includes compounds with receptor neutral antagonistic activity (neutral antagonists), receptor inverse agonistic activity (inverse agonists) and negative hormone activity (negative hormones) [Klein et al., J. biol. Chem. 271, 22692–22696 (1996)].

Thus, the term "retinoid antagonists" encompasses a) RXR antagonists of the formula I given earlier herein, particularly those of the formula

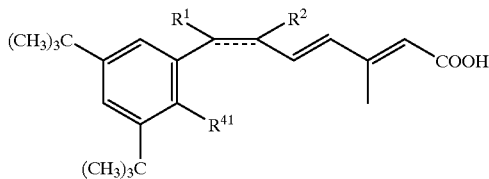

wherein the dotted bond is optional; and, when the dotted bond is present, $R^1$ is methyl and $R^2$ is hydrogen; and, when the dotted bond is absent, $R^1$ and $R^2$ taken together are methylene to form a cis-substituted cyclopropyl ring; and $R^{41}$ is $C_{1-4}$-alkoxy;

b) RAR α-antagonists of formulae

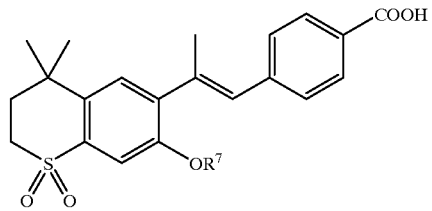

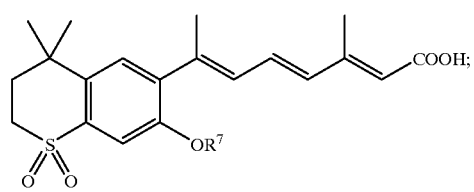

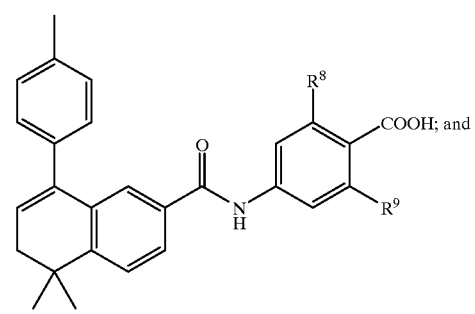

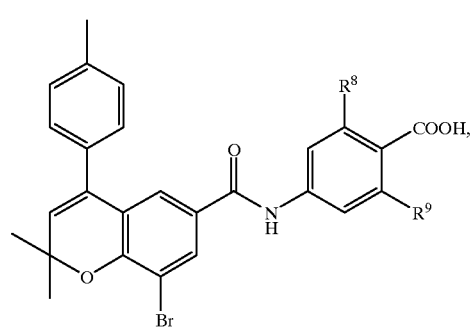

wherein $R^7$ is $C_{5-10}$-alkyl, and $R^8$ and $R^9$ independently of each other are hydrogen or fluorine;

such compounds being described in U.S. Pat. No. 5,391,766 and J. Med. Chem. 1997, 40, 2445;

c) RAR α,β antagonists of formulae

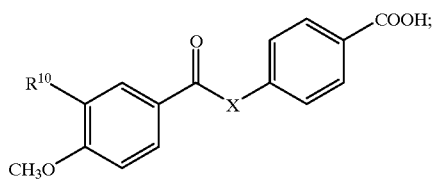

-continued

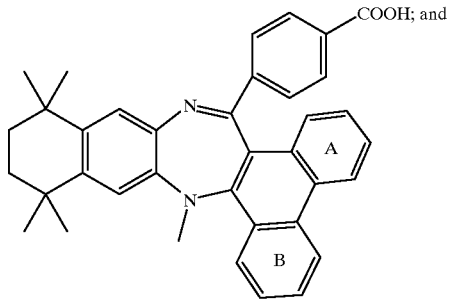
VIII

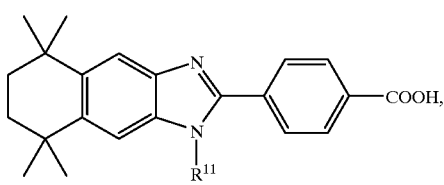
IX wherein $R_{10}$ is diamantyl, X is O or NH, $R^{11}$ is phenyl or benzyl, and wherein optionally either ring A or ring B is present;
such compounds being described in Med. Chem. Res. 1991, 1, 220; Biochem. Biophys. Res. Com. 1997, 231, 243; J. Med. Chem. 1994, 37, 1508;

d) RAR β,γ antagonists of formula

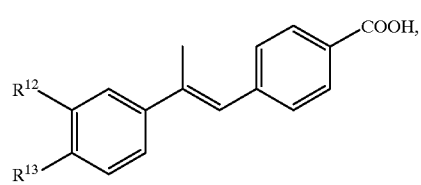
X wherein $R^{12}$ and $R^{13}$ independently of each other hydroxy, $C_{1-4}$-alkoxy, optionally branched C1–5-alkyl or adamantyl;
such compounds being described in J. Med. Chem. 1995, 38, 4993;

e) RAR γ antagonists of formulae

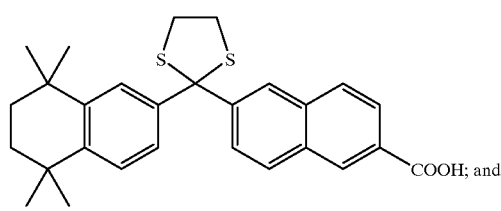
XI

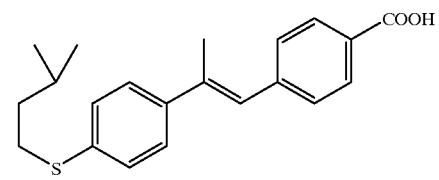
XII such compounds being described in Cancer Res. 1995, 55, 4446;

f) RAR α,β,γ antagonists of formulae

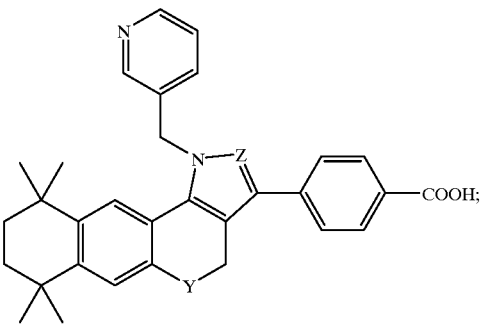
XIII

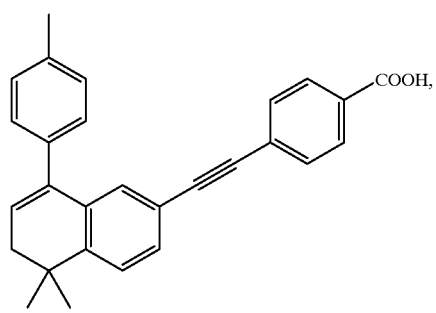
XIV

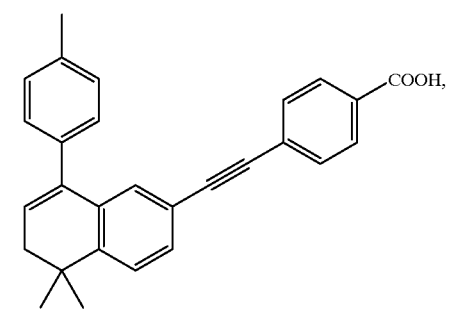
XV

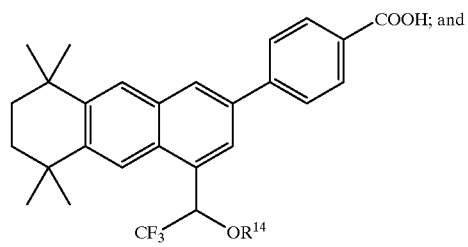
XVI wherein Y is —$CH_2$— or sulfur and Z is —CH= or nitrogen, and $R^{14}$ is hydrogen or $C_{1-4}$-alkyl;
such compounds being described in J. Med. Chem. 1995, 38, 3163 and 4764; J. Biol. Chem. 1996, 271, 11897 and 22692;

g) RXR antagonists of formula

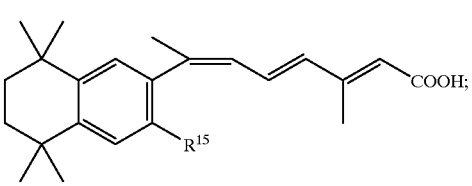
XVII wherein $R^{15}$ is $C_{1-4}$-alkoxy;

such compounds being described in J. Med. Chem. 1996, 39, 3229; and Nature 1996, 383, 450, as well as pharmaceutically acceptable salts and pharmaceutically acceptable hydrolyzable esters of the compounds of formulae III to XVII.

In the scope of the present invention, the "pharmaceutically acceptable salts" includes any salt chemically permissible in the art for retinoid antagonists and applicable to human patients in a pharmaceutically acceptable preparation. Any such conventional pharmaceutically acceptable salt of retinoid antagonists can be utilized. Among the conventional salts which can be utilized, there are the base salts included, for example, alkali metal salts such as the sodium or potassium salt, alkaline earth metal salts such as the calcium or magnesium salt, and ammonium or alkyl ammonium salts.

In accordance with this second aspect of the invention, it has thus been found that administration of retinoid antagonists, pharmaceutically acceptable salts, and pharmaceutically acceptable hydrolyzable esters thereof, are efficacious in treating patients with T-helper cell type 2 (Th2)-mediated diseases. It has also been found that the administration of retinoid antagonists is efficacious in treating patients with diseases mediated by Th2-related cytokines, such as interleukin-4 (IL-4) and IL-5. Thus, retinoid antagonists including but not limited to the compounds of formula I are all effective in treating Th2-mediated diseases.

This aspect of the invention, therefore, in one embodiment relates to the use of retinoid antagonists, their pharmaceutically acceptable salts or pharmaceutically acceptable hydrolyzable esters, for the manufacture of a medicament for the treatment of T-helper cell type 2 (Th2)-mediated immune diseases. In another embodiment this aspect of the invention relates to the use of retinoid antagonists, their pharmaceutically acceptable salts or pharmaceutically acceptable esters thereof for the manufacture of a medicament for the treatment of disease mediated by Th2-related cytokines, such as IL-4 and IL-5. In this respect the invention more particularly relates to a method for treating patients having T-helper cell type 2 (Th2)- mediated immune diseases comprising administering to said human patient a compound selected from the group of retinoid antagonists, pharmaceutically acceptable salts and pharmaceutically acceptable hydrolyzable esters thereof, said compound being administered in an amount effective to treat said disease. The term "treatment" or "treating" includes preventive and/or therapeutic treatment.

As used herein, the term, T-helper cell type 2-mediated immune diseases" relates to diseases involving immunoglobulin E (IgE) and mast cells due to the development and activation of allergen-specific Th2 cells and it encompasses allergic diseases, such as a topic dermatitis, other dermatological diseases associated with atopy; allergic rhinitis or hay fever, allergic bronchial asthma in its acute or chronic, mild or severe forms, with or without acute or chronic bronchitis. Elevated serum levels of immunoglobulin E (IgE) and hypereosino-philia can be associated with these diseases. Retinoid antagonists are effective in all those immune diseases which are linked with an increase of Th2 cell activity and an increased secretion of the related cytokines, such as IL-4 and IL-5. The therapeutic effect of retinoid antagonists is supposedly due to a decrease in Th2 cell activity, a decreased secretion of the related cytokines, such as IL-4 and IL-5, and/or an increase in Th1 cell activity due to the enhancement of IL-12 production by activated myelomonocytic cells. [S. Romagnani, Ann. Rev. Immunol. 12, 227–257 (1994); Romagnani, ed., Th1 and Th2 Cells in Health and Disease. Chem. Immunol., Karger, Basel, 63, pp. 187–203 (1996); Abbas et al., Nature 383, 787–793 (1996)].

The efficacy of the retinoid antagonists in accordance with the present invention can be shown by their ability to upregulate Th1 cell activity, induce/stimulate the production of the Th1-related cytokine IL-12, and to down-regulate Th2 cell activity and suppress the expression of Th2-related cytokines, such as IL-4 and IL-5 (see Examples 4 and 5 below).

Retinoid antagonists are active in the treatment of allergic bronchial asthma. The hallmarks of inflammation associated with asthmatic disease are the presence of activated eosinophils, an increased sensitivity of the airways (hyperresponsiveness), edema, mucus hypersecretion and cough. This inflammatory process is mediated by the generation and activation of Th2-type cells. The ability of retinoid antagonists, and in particular all of the compounds of formula I to promote a Th1-type response and thereby to suppress the Th2-type response is thought to be the mechanism underlying the efficacy of these compounds in allergic lung inflammation/asthma. Retinoid antagonists are acting on Th1-type cells, in inhibiting the signs and symptoms of allergic lung inflammation/asthma [Gavett et al., J. exp. Med. 182, 1527–1536 (1995); Kips et al., Am. J. Respir. Crit. Care Med. 153, 535–539 (1996)]. They are active in antigen/allergen (e.g. ovalbumin)-sensitized and challenged animals. Retinoid antagonists, given either systemically or topically by aerosol, are efficacious in attenuating, inhibiting or reversing bronchoconstriction, airway edema and mucus hypersecretion, airway inflammation, accumulation of eosinophils and neutrophils in the broncho-alveolar tissue and broncho-alveolar lavage respectively, as well as airway hyperresponsiveness to non-specific stimuli (see Example 6 below).

For the treatment, the active compound, i.e. a retinoid antagonist, a pharmaceutically, acceptable salt or a pharmaceutically acceptable hydrolyzable ester thereof, is administered either systemically or topically. Preferably, said compound is administered as a composition containing said active compound and a pharmaceutically acceptable carrier or diluent compatible with said active compound. In preparing such composition, any conventional pharmaceutically acceptable carrier can be utilized. When the drug is administered orally, it is generally administered at regular intervals, conveniently at mealtimes or once daily. It has been established that this compound is effective in doses which show no or only mild side effects when given orally or when given topically. Therefore, oral or topical administration of the active compound is generally preferred. For treating diseases of the skin, mouth, nose, pharynx, larynx, bronchus etc. oral combined with topical administration may also be used advantageously.

In a third aspect of this invention, it has been found that administration of retinoid antagonists, pharmaceutically acceptable salts, and pharmaceutically acceptable hydrolyzable esters thereof, are efficacious in treating patients with osteoporosis.

The invention, therefore, in that aspect, relates to the use of retinoid antagonists, their pharmaceutically acceptable salts or pharmaceutically acceptable hydrolyzable esters, for the manufacture of a medicament for the treatment of osteoporosis.

Accordingly, the invention also relates to a method for treating patients having osteoporosis comprising administering to said human patient a compound selected from the group of retinoid antagonists, pharmaceutically acceptable salts and pharmaceutically acceptable hydrolyzable esters thereof, said compound being administered in an amount effective to treat said disease. The term "treatment" or "treating" includes preventive and/or therapeutic treatment.

With reference to that aspect of the invention the term "retinoid antagonists" encompasses the groups a) to g) of compounds as defined earlier herein.

As used herein the term "osteoporosis" includes primary as well as secondary osteoporosis and relates to a disease characterized by a low bone mass and a micro-architectural deterioration of bone tissue leading to enhanced bone fragility and a consequent increase in bone fracture risk.

The two most common forms of primary osteoporosis are: 1. The postmenopausal osteoporosis in women (osteoporosis type I) with a high rate of bone remodeling, also called high turnover form of osteoporosis. The increased resorption of trabecular bone leads most often to vertebral and wrist fractures. 2. Senile osteoporosis in individuals of both sexes mostly over 70 years (osteoporosis type II) with a low rate of bone remodeling called low turnover form of osteoporosis. The increased resorption of both trabecular and cortical bone leads frequently to fractures of vertebrae and femoral neck.

Secondary osteoporosis is related to many conditions such as diseases (e.g. rheumatoid arthritis, tumor-induced osteolysis with or without hypercalcemia, intestinal and renal disorders), immobilisation/lack of exercise, malnutrition, disorders of calcium intake or vitamin D intake and their metabolism, disorders of parathyroid hormone metabolism, and drug therapy (e.g. corticosteroids, heparin).

The efficacy of retinoid antagonists in accordance with the present invention can be shown by their ability to influence bone remodeling, a process resulting from bone resorption. and bone formation. Bone resorption is mainly accomplished by multinucleated osteoclasts endowed with specialized organelles and plasma membrane structures to allow resorption of inorganic substances as well as organic matrix components. Bone formation is mainly a function of osteoblasts that build up the extracellular matrix consisting of proteoglycans, type I collagen, non-collagen proteins, osteonectin, osteocalcin and other components. A further function of osteoblasts is bone mineralization, involving induction of certain enzymes (e.g. alkaline phosphatase), incorporation of calcium and other components into the inorganic bone structure, such as hydroxyapatite.

When bone resorption rate is higher than bone formation, it leads to a net reduction in bone mass, which occurs in osteoporosis. Retinoid antagonists decrease bone resorption and/or increase bone formation and are therefore useful in prevention and therapy of osteoporosis.

Under physiological and pathological conditions a series of compounds are known to influence and particularly induce or stimulate bone resorption such as hormones, vitamines, growth factors, cytokines, prostaglandins, lipopolysaccharide etc. (Reviews are given in the book Principles of Bone Biology, Eds. J. B. Bilezikian et al., Academic Press, San Diego 1996: Horowitz M C et al., Local regulators of bone, pp. 687–700. Pilbeam C C et al., Prostaglandins and bone metabolism, pp. 715–728. Mundy G R, Role of cytokines, parathyroid hormone and growth factors in malignancy, pp. 827–836. Rodan G A et al., Pathophysiology of osteoporosis, pp. 979–990. Jones G, Pharmacological mechanism of therapeutics: Vitamin D and analogs, pp. 1069–1081. Hakeda et al., The growth and culture of bone cells: Osteoclastic, pp. 1217–1228. Geddes A D, Animal models of bone diseases, pp. 1343–1354).

The following compounds known as inducing/stimulating bone resorption were examined: Parathyroid hormone (PTH), parathyroid hormone related peptide (PTHrP), calcitriol (1,25-dihydroxyvitamin $D_3$), all-trans retinoic acid (all-trans RA), 9-cis retinoic acid (9-cis RA), prostaglandin E 2(PGE2), tumor necrosis factor α (TNFα), and interleukin-1α (IL-1α); Vaes G, Cellular biology and biological mechanism of bone resorption, Clinical Orthopaedics and related Research, 1988, 231, 239–271. Houghs S. et al., Effects of hypervitaminosis A on the bone and mineral metabolism of the rat, Endocrinology 1988, 122, 2933–2939. Tullberg-Reinert H. et al., Different inhibitory actions of cyclosporin A and cyclosporin A-acetate on lipopolysaccharide-, interleukin 1-, 1,25-dihydroxyvitamin $D_3$-, and. parathyroid hormone-stimulated calcium and lysosomal enzyme release from mouse calvaria in vitro. Agents and Actions 1991, 32, 321–332. Ammann P. et al., Effects of the biphosphonale tiludronate on bone resorption, calcium balance and bone mineral density. J. Bone Miner. Res. 1993, 8, 1491–1498. Bonjour J P et al., Tiludronate: Bone pharmacology and safety. Bone 1995, 17, 473S-477S. Kindmark A et al., Inhibitory effects of 9-cis and all-trans retinoic acid on $1,25(OH)_2$ vitamin $D_3$-induced bone resorption Calcif. Tissue Int. 1995, 57, 242–244. Saneshige S., Retinoic acid directly stimulates osteoclastic bone resorption and gene expression of cathepsinK/OC-2. Biochem. J. 1995, 309, 721–724.

It could be demonstrated that retinoid antagonists inhibit bone resorption induced by above mentioned resorption stimulating compounds. This was proven in the widely used model of neonatal mouse calvaria (skull bones) tissue culture, a model predictive for agents useful in clinical prevention and therapy of osteoporosis e.g. biphosphonates. The experiments are described below in Example 7.

In a fourth aspect the present invention relates to the use of retinoid antagonists comprising retinoids with selective retinoic acid receptor (RAR) antagonist activity, retinoid X receptor (RXR) antagonistic activity, or mixed RAR-RXR antagonistic activity for use in the treatment of preneoplastic and neoplastic diseases such as precancerous lesions of the skin and mucous membranes, or solid tumors of skin, mucous membranes, head and neck, lung, stomach, colon, breast, ovary, cervix and prostate; and in the manufacture of a medicament for the treatment of such diseases (see Example 8 below).

For the treatment of the above-mentioned diseases, the active compound, i.e. a retinoid antagonist, a pharmaceutically acceptable salt or a pharmaceutically acceptable hydrolyzable ester thereof, is administered either systemically or topically. Preferably, said compound is administered as a composition containing said active compound and a pharmaceutically acceptable carrier or diluent compatible with said active compound. In preparing such composition, any conventional pharmaceutically acceptable carrier can be utilized. When the drug is administered orally, it is generally administered at regular intervals, conveniently at mealtimes or once daily. It has been established that this compound is effective in doses which show no or only mild side effects when given orally or when given topically. Therefore, oral or topical administration of the active compound is generally preferred. For treating diseases of the skin, mouth, nose, pharynx, larynx, bronchus etc. oral combined with topical administration may also be used advantageously.

In the treatment of the above-mentioned diseases, retinoid antagonists, when administered orally do not or only slightly induce the adverse events belonging to the toxic syndrome of hypervitaminosis A, such as mucocutaneous, musculoskeletal, neurologic manifestations and elevation of transaminases, triglycerides and cholesterol. In addition, they are not or less teratogenic in contrast to the receptor agonistic retinoids clinically useful in the treatment of dermatological and oncological diseases, such as all-trans retinoic acid (tretinoin), 13-cis retinoic acid (isotretinoin), etretinate and acitretin.

In the treatment of T-helper cell type 2-mediated immune diseases, retinoid antagonists, pharmaceutically acceptable salts or pharmaceutically acceptable hydrolyzable esters thereof, can be used alone or in combination with other measures, e.g. in combination with other pharmaceutically active substances such as topical or systemic corticosteroids, antihistaminics and bronchodilating agents. If used in combination with other substances, retinoid antagonists and said other substances can be administered separately or incorporated in effective amounts into one pharmaceutical composition.

In the treatment of osteoporosis, retinoid antagonists, pharmaceutically acceptable salts or pharmaceutically acceptable hydrolyzable esters thereof, can be used alone or in combination with other measures, e.g. in combination with other pharmaceutically active substances such as calcium, vitamin D derivatives, estrogens, anabolics, calcitonin or biphosphonates. If used in combination with other substances, retinoid antagonists and said other substances can be administered separately or incorporated in effective amounts into one pharmaceutical composition.

In accordance with this invention the retinoid antagonists can also be administered in the form of its pharmaceutically acceptable hydrolyzable esters. Any pharmaceutically acceptable hydrolyzable ester can be used in the compositions and methods of this invention. Among the preferred esters are: the aromatic esters such as benzyl esters in which the benzyl moiety is unsubstituted or substituted with lower alkyl, halo, nitro, thio, or substituted thio; or lower alkyl esters, e.g. ethyl, t-butyl, cyclopentyl, cyclohexyl or cycloheptyl ester; or 9-fluorenylmethyl ester.

The aforementioned retinoid antagonists, the salts and esters thereof are useful especially in pharmaceutically acceptable oral or topical modes. These pharmaceutical compositions contain said active compound in association with a compatible pharmaceutically acceptable carrier material. Any conventional carrier material can be utilized. The carrier material can be organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutically active preparations may contain other pharmaceutically active agents. Additionally, additives such as flavouring agents, preservatives, stabilizers, emulsifying agents, buffers and the like may be added in accordance with accepted practices of pharmaceutical compounding.

The pharmaceutical preparations can be made up in any conventional form including inter alia: (a) a solid form for oral administration such as tablets, capsules (e.g. hard or soft gelatine capsules), pills, sachets, powders, granules, and the like; (b) preparations for topical administrations such as solutions, suspensions, ointments, creams, gels, micronized powders;, sprays, aerosols and the like. The pharmaceutical preparations may be sterilized and/or may contain adjuvants such as preservatives, stabilizers, wetting agents, emulsifiers, salts for varying the osmotic pressure and/or buffers.

For topical administration to the skin or mucous membrane the aforementioned derivative is preferably prepared as ointments, tinctures, creams, gels, solution, lotions, sprays; aerosols and dry powder for inhalation, suspensions, shampoos, hair soaps, perfumes and the like. In fact, any conventional composition can be utilized in this invention. Among the preferred methods of applying the composition containing the agents of this invention is in the form of an ointment, gel, cream, lotion, spray, aerosol or dry powder for inhalation. The pharmaceutical preparation for topical administration to the skin can be prepared by mixing the aforementioned active ingredient with non-toxic, therapeutically inert, solid or liquid carriers customarily used in such preparation. These preparations generally contain 0.01 to 5.0 percent by weight, preferably 0.1 to 1.0 percent by weight, of the active ingredient, based on the total weight of the composition.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-α-tocopherolamine, tocopherols, butylated hydroxyanisole, butylated hydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, ethylene glycol and an emulsifying agent.

Ointment formulations containing the active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components function as a stabilizer. These fatty acid alcohol components are derived from the reduction of a long-chain saturated fatty acid containing at least 14 carbon atoms. Also, conventional perfumes and lotions generally utilized in topical preparation for the hair can be utilized in accordance with this invention. Furthermore, if desired, conventional emulsifying agents car be utilized in the topical preparations of this invention.

For topical treatment of allergic rhinitis and allergic bronchial asthma nasal and inhalation aerosols are used. Formulations for such aerosols are described in Drugs and Pharmaceutical Sciences, Marcel Dekker, New York, 1996, Vol. 72, pp. 547–574. Furthermore, the active compound can be delivered by dry powder inhalation. Such formulations and devices are described in Pharmaceutical Technology, June 1997, pp. 117–125.

A preferred oral dosage form comprises tablets, pills, sachets, or capsules of hard or soft gelatin, methylcellulose or of another suitable material easily dissolved in the digestive tract. Each tablet, pill, sachet or capsule can preferably contain from about 5 to about 200 mg, more4 preferably from about 20 to about 100 mg, of active ingredient. The oral dosages contemplated in accordance with the present invention will vary in accordance with the needs of the individual patient as determined by the prescribing physician. Generally, however, a daily dosage of from 0.05 to 20 mg per kg of body weight, preferably 0.1 to 7 mg, and most preferably from about 0.3 mg to about 1.5 mg per kg of body weight of the patient is utilized. This dosage may be administered according to any dosage schedule determined by the physician in accordance with the requirements of the patient.

The dosage for treatment typically depends on the route of administration, the age, weight and disease condition of the individual. Suitable dosage forms are known in the art or can be easily obtained in a manner known per se. Formulations of lotions, gels, creams, sprays; aerosols and dry powder for inhalation, hard or soft gelatin capsules, tablets and sachets that are particularly suitable in the scope of the present invention or that can be easily adjusted in accordance with the above teaching are in the art.

The pharmacological activity of the retinoid antagonists as disclosed above can be demonstrated in various test models as shown below in Examples 1–8. In Examples 1–8 the following compounds were used:

Compound A: (2E,4E,6Z)-7-[3,5-di-tert.butyl-2-ethoxyphenyl]3-methyl-2,4,6-octatrienoic acid Compound B: (2E,4E,6Z)-7-[3,5-di-tert.butyl-2-butyloxyphenyl]-3-methyl-2,4,6-octatrienoic acid Compound C: all-trans retinoic acid Compound D: 13-cis retinoic acid Compound E: 9-cis retinoic acid Compound F: 4-(5,6,7,8-tetrahydro-5,5,8,8-tetramethyl-2-naphthalene-carboxamido)benzoic acid Compound G: (2E,4E)-3-methyl-5-[(1S,2S)-2-(5,5,8,8-tetramethyl-5,6,7,8-tetrahydro-naphthalen-2-yl)-cyclopropyl]-penta-2,4-dienoic acid Compound H: p-[(E)-2-[3',4'-Dihydro-4',4'-dimethyl-7'-(heptyloxy)-2'H-1-benzothiopyran-6'-yl]propenyl] benzoic acid 1',1'-dioxide Compound I: 4-(7,7,10,10-Tetramethyl-1-pyridin-3-ylmethyl-4,5,7,8,9,10-hexahydro-1H-naphto[2,3-g] indol-3-yl)-benzoic acid

EXAMPLE 1

Effect of retinoids with RXR antagonistic activity on weight loss induced by all-trans retinoic acid in mice.

The test compounds were solubilized/suspended in arachis oil and applied intraperitoneally into female mice (25/30 g) for 5 days a week during 2 weeks. The results are shown in Table 1.

TABLE 1

| Compound/<br>Dose [mg/kg] | C/200<br>n = 2 | C/200 +<br>A/200<br>n = 2 | C/100<br>n = 10 | C/100 +<br>A/200<br>n = 2 | A/200<br>n = 2 |
|---|---|---|---|---|---|
| % survival after 14 days | 0 | 100 | 20 | 100 | 100 |
| % weight change after 4 days | −38 | −23 | −18 | −13 | +15 |
| % weight change after 7 days | dead | −23 | −29 | −8 | +26 |

EXAMPLE 2

Suppressive effect on skin irritation caused by all-trans retinoic acid in hairless rats.

The animals were treated epicutaneously (0.025 ml/2 cm$^2$) once a day, 5 days a week (Monday to Friday) for 4 consecutive weeks with the mixed solution of the test compounds in acetone/ethanol (1/1).

The animals were observed daily, Monday to Friday, for signs of erythema and oedema on each individual test site, starting at approximately 24 hours after initiating the study. The intensity of all skin reactions induced was recorded in the raw data sheets according to the following grading scale:

0=No skin reactions

1=Slight skin reactions (slight to defined erythema)

2=Well defined reaction (well defined to marked erythema)

3=Moderate skin reaction (moderate to marked erythema with defined oedema)

4=Severe skin reaction (severe to strong erythema and marked oedema)

The mean cumulative skin irritation scores calculated after each treatment application are presented in FIGS. 1 and 2.

EXAMPLE 3

Suppressive effect on the in vitro teratogenic activity of various retinoids.

Fore- and hindlimb buds of day 13 rat embryos were dissociated in calcium-magnesium-free balanced salt solution containing 0.1% trypsin and 0.1% EDTA at 37° C. The cell density was adjusted to $2\times10^7$ limb bud cells/ml in CMRL medium containing 10% NU-serum. High cell density cultures were set up by dispensing 20 µl of the cell suspension as a discrete drop in the center of each well of a 24-well dish. The cells were allowed to attach for 1–2 h at 37° C. before the cultures were flooded with the appropriate culture medium. The test substances then were dissolved in dimethylsulfoxide and added at the same time on day 1 of culture. An equivalent amount of the solvent (0.4%) was added to the control cultures. After 7 days in culture the grade of differentiation of mesenchymal cells into chondrocytes, producing cartilage was determined by staining proteoglycans with alcian blue. The bound dye was extracted with 4 M guanidine hydrochloride and the absorbance at 600 nm was determined spectrophotometrically.

FIG. 3 shows the interaction of variable concentrations of Compound A with a constant concentration of all-trans retinoic acid (Compound C). C was kept during the experiment at a constant concentration of $1\times10^{-6}$ mol/l. The concentrations of Compound A increased from $1\times10^{-9}$ mol/l to $2\times10^{-6}$ mol/l. The differentiation of the mesenchymal cells increased from about 5% to about 30% with increasing concentrations of Compound A.

EXAMPLE 4

Figure 1:
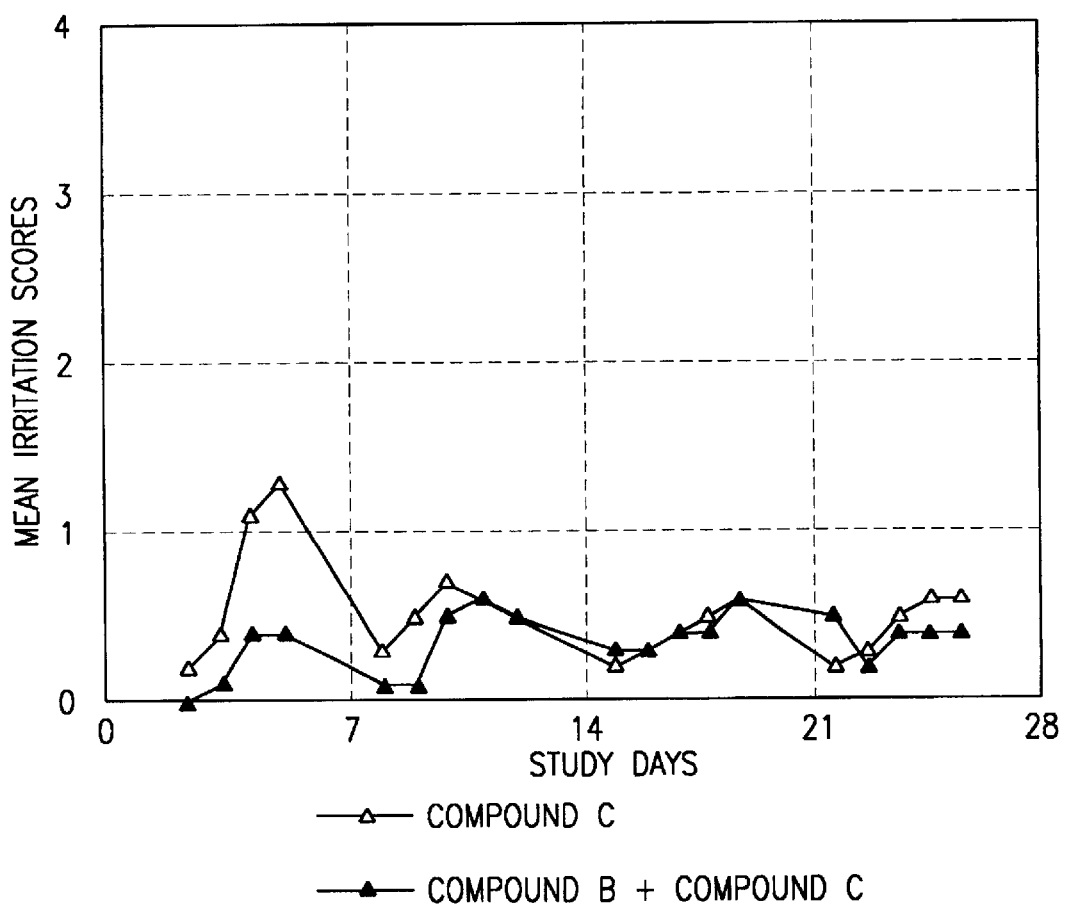
Figure 2:
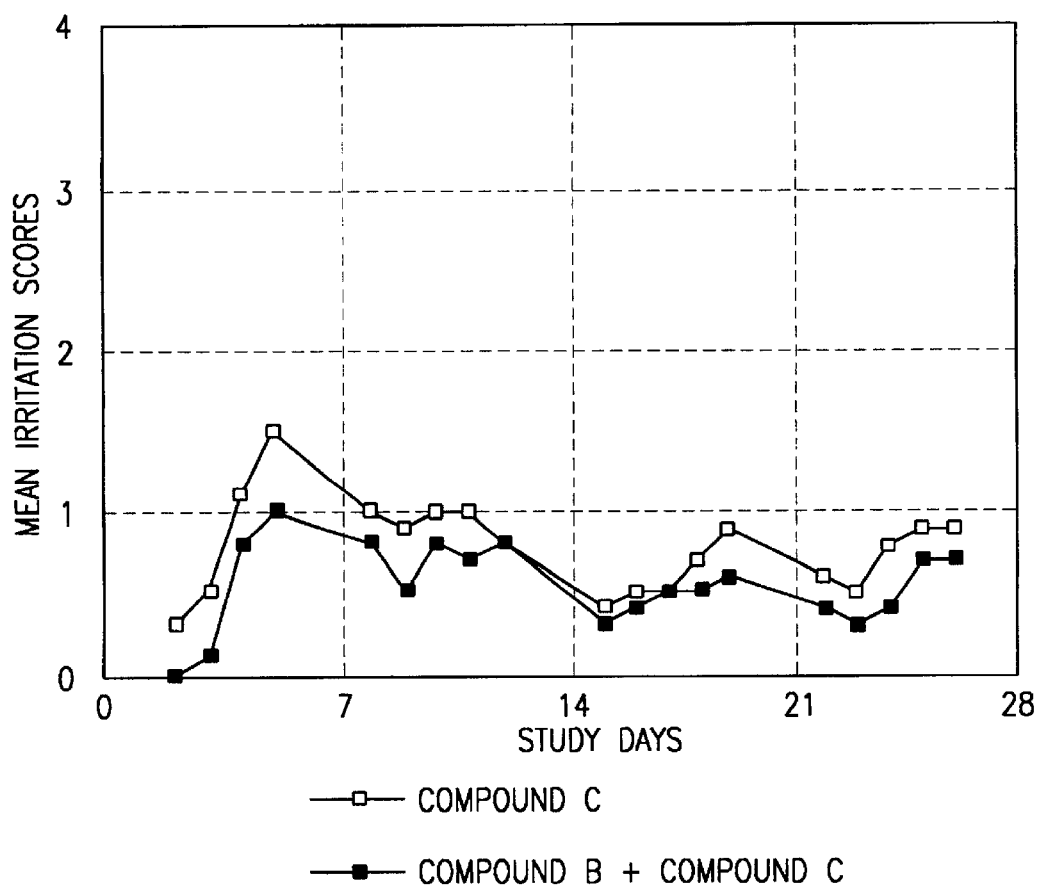
Figure 3:
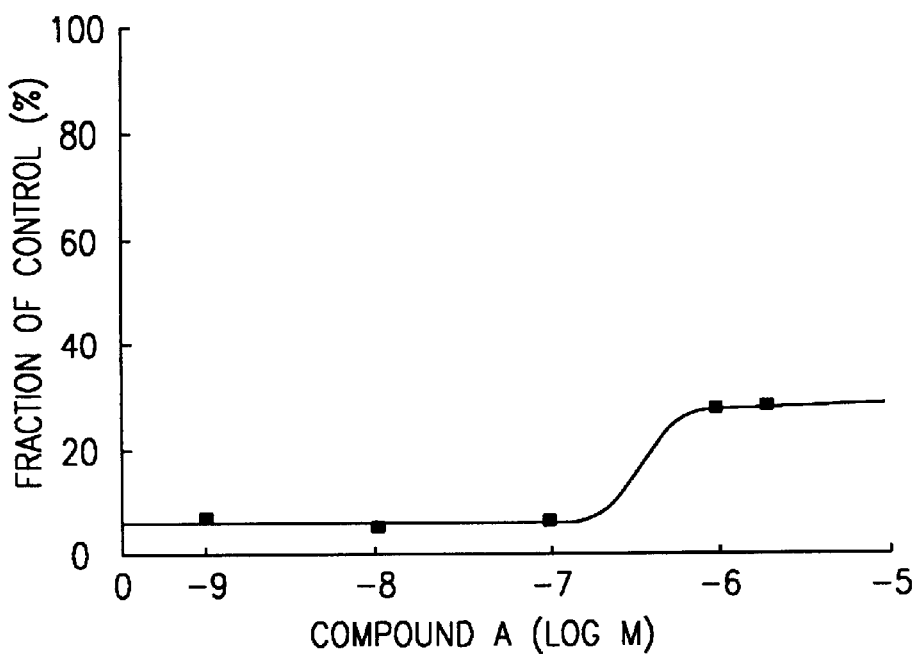
Figure 4:
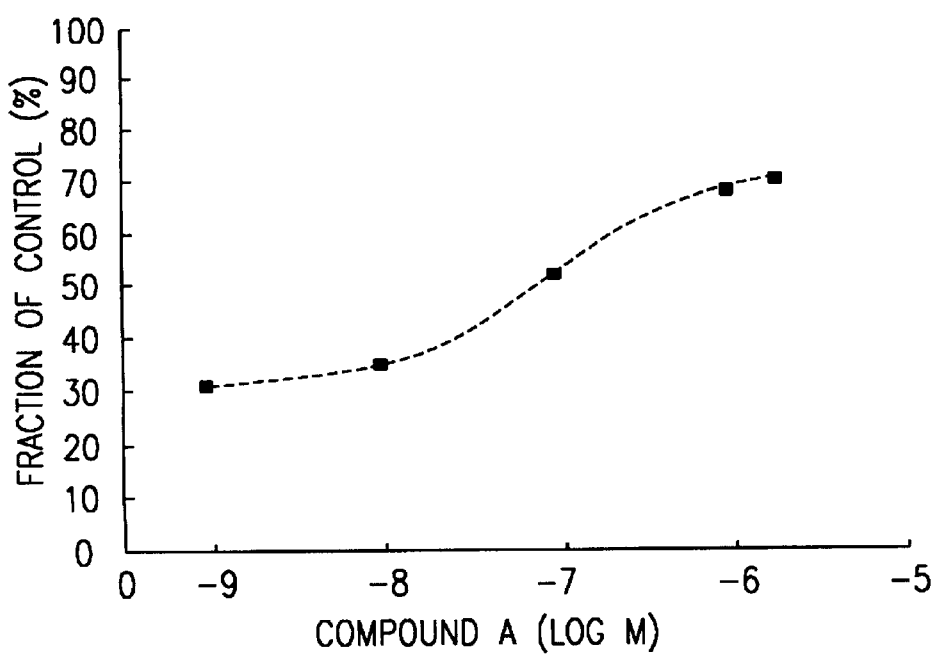
FIG. 4 shows the interaction of variable concentrations of Compound A ($1\times10^{-9}$ mol/l to $2\times10^{-6}$ mol/l) with Compound D which was kept during incubation at the constant concentration of $1\times10^{-6}$ mol/l. The differentiation of the mesenchymal cells increased from about 30% to about 70% with increasing concentrations of Compound A.
Figure 5:
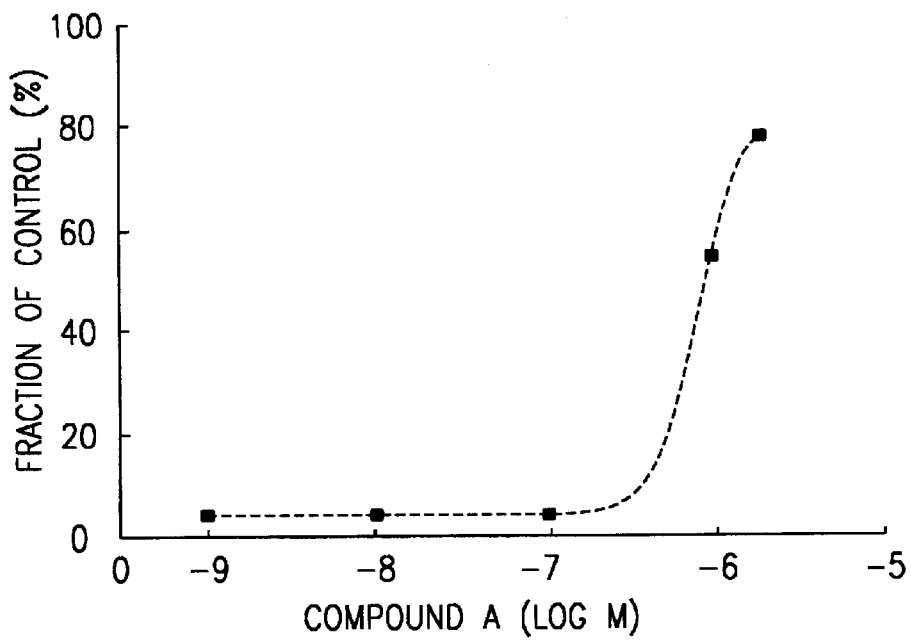
FIG. 5 shows the interaction of variable concentrations of Compound A ($1\times10^{-9}$ mol/l up to $2\times10^{-6}$ mol/l with Compound E, which was kept during incubation at the constant concentration of $5\times10^{-7}$ mol/l. The differentiation of the mesenchymal cells increased from about 5% to about 80% with increasing concentrations of Compound A.
Figure 6:
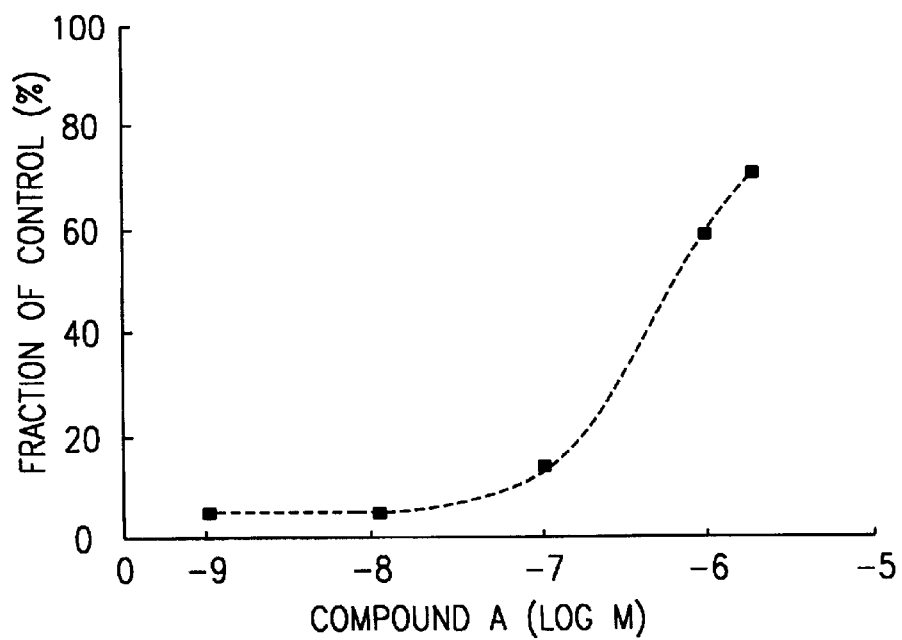
FIG. 6 shows the interaction of variable concentrations of Compound A ($1\times10^{-9}$ mol/l up to $2\times10^{-6}$ mol/l) with Compound F which was kept during incubation at the constant concentration of $1\times10^{-8}$ mol/l. The differentiation of the mesenchymal cells increased from about 5% to about 75% with increasing concentrations of Compound A.
Figure 7:
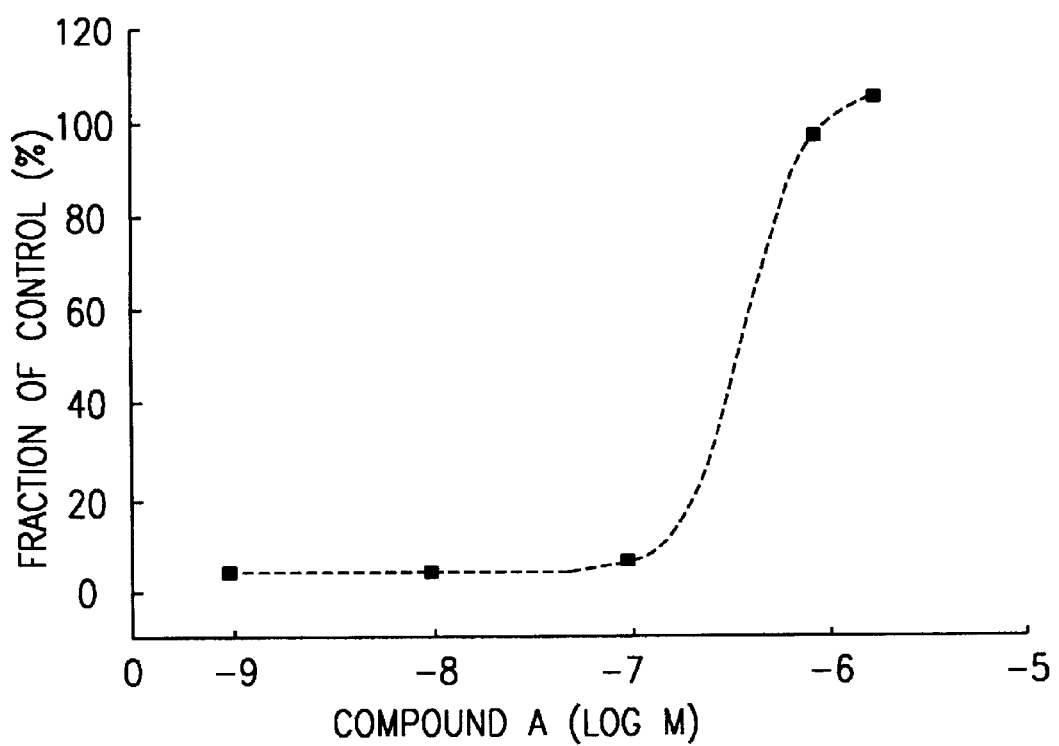
FIG. 7 shows the interaction of variable concentrations of Compound A ($1\times10^{-9}$ mol/l up to $2\times10^{-6}$ mol/l) with Compound G, which was kept during incubation at the constant concentration of $1\times10^{-6}$ mol/l. The differentiation of the mesenchymal cells increased from about 5% to about 110% with increasing concentrations of Compound A.

In vitro assay for induction of IL-12 production by retinoid antagonists

THP-1 cells were obtained from American Tissue Culture Collection and cultured in complete medium. To assay for IL-12 production, THP-1 cells, $1.25\times10^6$ cells/ml, were stimulated with *S. aureus* Cowan strain (SAC) (1/1000) and human recombinant interferon-γ (huIFN-γ (1000 U/ml) [Ma et al., *J. Exp. Med.* 183, 147–157 (1996)]. Alternatively, $0.5\times10^6$ human peripheral blood mononuclear cells (PBMC) (1 ml culture in 48 well plates) were primed with huIFN-γ (1000 U/ml) for 16 hours at 37° C., and then stimulated with SAC (1/1000). Supernatants were collected after 48 hours and freezed at −20° C. until assayed [Panina-Bordignon et al., *J. Clin. Invest.* 100, 1513–1519 (1997)].

IL-12 production was measured by specific enzyme linked immuno sorbant assay (ELISA), using 20C2 antibody (rat anti human IL-12 heterodimer p40–p35), at 2.5 μg/ml in coating buffer, and peroxidase-conjugated 4D6 antibody (rat anti human IL-12) at 250 ng/ml in assay buffer as described [Zhang et al., *J. Clin. Invest.* 93, 1733–1739 (1994)]. Standard (recombinant human IL-12, 800 pg/ml to 6 pg/ml) and samples (100 μl) diluted in assay buffer were added to duplicate wells. Absorbance was read at 450–650 nm. The unknown IL-12 concentrations of the samples were read from the corresponding standard curve and multiplied by the corresponding dilution factor. Maximal IL-12 production varied between 200 and 400 pg/ml.

Lyophilized retinoid antagonists were diluted in DMSO under yellow light, on ice at a concentration of 2 mM. Serial dilutions (1 μM–1 pM) were prepared in complete RPMI medium. 10 μl of each dilution was added to 1 ml culture.

The results of the experiments indicate that the tested retinoid antagonists influence IL-12 production. In particular, the tested tetinoid antagonists stimulate IL-12 production by activated human monocytes, see Table 2 and 3.

TABLE 2

Retinoid antagonists specifically enhance IL-12 production by activated monocytes

|  | nM | IL-12 (pg/ml) | IL-10 (pg/ml) | TNF-α (pg/ml) |
|---|---|---|---|---|
| medium |  | 0 | <10 | <10 |
| SAC + IFN-γ |  | 120 | 1040 | 1840 |
| RAR α antagonist | 1000 | 251 | 1343 | 1912 |
| Compound H | 100 | 102 | 1050 | 1600 |
|  | 10 | n.d. | 1060 | 1392 |
| medium |  | 0 | <10 | <10 |
| SAC + IFN-γ |  | 126 | 1040 | 2000 |
| RAR α,β,γ antagonist | 1000 | 321 | 1116 | 2884 |
| Compound I | 100 | 205 | 983 | 2752 |
|  | 10 | 173 | 971 | 2592 |
| medium |  | 0 | <10 | <10 |
| SAC + IFN-γ |  | 120 | 1040 | 1840 |

TABLE 2-continued

Retinoid antagonists specifically enhance IL-12 production by activated monocytes

|  | nM | IL-12 (pg/ml) | IL-10 (pg/ml) | TNF-α (pg/ml) |
|---|---|---|---|---|
| RXR antagonist | 1000 | 298 | 1700 | 1560 |
| Compound B | 100 | 161 | 1521 | 1812 |
|  | 10 | 106 | 1020 | 1484 |

TABLE 3

Retinoid antagonists enhance IL-12 production by PBMC and THP-1 cells that have been primed with IFNγ and stimulated with SAC

| Compound | Receptor Specificity | Activity | Stimuli | Time* (hrs) | PBMC IL-12 | THP-1 (pg/ml) |
|---|---|---|---|---|---|---|
| H | RAR α | antagonist | IFNγ + | 0 | 503 | 306 |
|  |  |  | SAC | 16 | 401 | nd |
| I | RAR α,β,γ | antagonist | IFNγ + | 0 | 371 | 364 |
|  |  |  | SAC | 16 | 367 | nd |
| B | RXR | antagonist | IFNγ + | 0 | 568 | 577 |
|  |  |  | SAC | 16 | 367 | nd |
| none |  |  | none |  | <12 | <2 |
|  |  |  | IFNγ + |  | 360 | 275 |
|  |  |  | SAC |  |  |  |

*retinoid antagonists (1 μg) were added at time 0 together with IFNγ or after 16 hours together with SAC.

EXAMPLE 5

In vitro assay for inhibition of differentiation of human naive T cells into T helper 2 (Th2) cells by retinoid antagonists.

Naive T cells from cord blood were isolated and treated as described [Panina-Bordignon et al. *J. Clin. Invest.* 100. 1513–1519 (1997)). Briefly, cord blood derived mononuclear cells were incubated with anti-CD45RA and anti-CD4 monoclonal antibodies. After a 20 minute incubation, cells were washed and incubated with goat anti-mouse Ig-coated magnetic beads. Positive cells were separated and seeded at $1\times10^6$ cells/ml in a 24 well plate, together with autologous adherent cells, PHA, and IL-4 in the presence or absence of Compound H or Compound B at 1 mM for 5 days. Cells were then washed and put back in culture in the presence of IL-2 (100 U/ml). After 10 days, the cells were collected and restimulated with PMA (50 ng/ml) and ionomycin (1 μg/ml) for 4 hours. Brefeldin A (10 μg/ml) was added for the last 2 hours. Then the cells were fixed with 4% paraformaldehyde and permeabilized with saponin. Fixed cells were stained with FITC-anti IFNγ and PE-anti-IL-4mAbs and subjected to cytofluorimetric analysis.

The results of the experiment indicate that the tested retinoid antagonists reduce the differentiation of naive T cells into IL-4-secreting Th2 cells. (Table 4)

TABLE 4

Suppression of IL-4 expression in Th2 cells by retinoid antagonists

|  | IL-4 expressing cells | |
|---|---|---|
|  | % gated cells | % Th2 cells |
| Th2 | 26.32 | 100 |
| Th2 + Compound H | 10.8 | 41 |
| Th2 + Compound B | 8.5 | 32 |

EXAMPLE 6

Murine model of allergen-induced airway inflammation and hyperresponsiveness.

C57BL/6 mice (8–9 weeks old) are actively sensitized to ovalbumin (OA) on day 0 and on day 14 by a intraperitoneal injection of 10 μg OA+1 mg Al(OH)$_3$ (gel suspension) in 0.2 ml sterile saline. On day 21, the mice were challenged with 5.0% OA aerosol for 18 minutes. The aerosol is generated by a De Vilbiss Ultra-Neb 90 ultrasonic nebulizer, the outlet of which is connected to a small plexiglass chamber containing the animals. The mice are dosed with the RXR antagonist Compound B (10 and 30 mg/kg intraperitoneally) daily for three days, 48 hours, 24 hours, and immediately prior to OA challenge. Animals are used on day 21.

Airway Inflammatory Cell Accumulation: On day 24, three days after the challenge with OA aerosol, animals are anesthetized with urethane (2.4 g/kg) and tracheotomized with a 23 gauge catheter. Lungs are lavaged with aliquots (2×1 ml) of sterile Hank's balanced salt solution without $Ca^{++}$ and $Mg^{++}$. Lavage fluid is recovered after 30 sec by gentle aspiration and pooled for each animal. Samples then are centrifuged at 2000 rpm for 15 minutes at 5° C. Red blood cells are lysed from the resulting pellet with 0.5 ml distilled water and the cells remaining in the pellet are reconstituted with 5 ml HBSS. Samples are centrifuged a second time at 2000 rpm for 15 minutes at 5° C. The resulting pellet is suspended in 1 ml of HBSS. Total cell number is determined from an aliquot of the cell suspension using a hemocytometer. For cytological preparations, the cells are fixed on cytocentrifuged slides stained with a modified Wright's stain. Differential counts on at least 300 cells are made using standard morphological criteria to classify cells.

The results of the experiments indicate that the tested retinoid antagonists inhibit the allergen-induced accumulation of airway inflammatory cells (Table 5)

TABLE 5

Suppression of airway inflammatory cell accumulation by retinoid antagonists in a mouse model of allergen-induced airway inflammation

|  | Cell Influx (cells/ml) | | | Percent of reduction | |
|---|---|---|---|---|---|
|  |  | Compound B | | Compound B | |
|  | Vehicle | 10 mg/kg | 30 mg/kg | 10 mg/kg | 30 mg/kg |
| Total leukocytes | 795000 | 488000 | 271000 | 39% | 66% |
| Macrophages | 443000 | 289000 | 172000 | 35% | 62% |
| Eosinophils | 335000 | 176000 | 91000 | 48% | 73% |

Airway Hyperresponsiveness

On day 24, three days after the challenge with OA aerosol, animals are anesthetized with pentobarbital sodium (100 mg/kg, i.p.) and tracheotomized (PE-190). A jugular vein is cannulated with a sylastic tubing for i.v. drug delivery. Animals are placed in a whole body plethysmograph with a built-in pneumotachograph and mechanically ventilated ($V_f$=150/min., $V_t$=0.3 ml; Model 683, Harvard Apparatus, S. Natic, Mass.) immediately following pancuronium bromide (0.1 mg/kg, i.v.) treatment. Tidal volume is obtained from an integration of the respiratory flow signal using a differential pressure transducer (Validyne DP 103–08, Northridge, Calif.). Transpulmonary pressure is measured with a differential pressure transducer (Validyne DP 45–30, Northridge, Calif.) as the difference between intratracheal pressure and intrapleural pressure (obtained from a cannula inserted into the intercostal space). Changes in lung resistance (cm $H_2O$/ ml/s) to increasing doses of methacholine (30, 100, 300, 1000 μg/kg, i.v.) are calculated from transpulmonary pressure, tidal volume, and respiratory flow measurements using a Modular Instrument Signal Processing System (Malvern, Pa.).

The results of the experiments indicate that retinoid antagonists can prevent or reverse allergic airway inflammation and inhibit antigen-induced bronchoconstriction, typical for allergic airway diseases, such as allergic bronchial asthma.

EXAMPLE 7

Examples for the Effect of Retinoid Antagonists on Bone Resorption.

Bone Resorption Assay

A series of agents are known to induce or stimulate bone resorption. In this assay retinoid antagonists were tested for their capacity to inhibit or counteract the bone resorptive activity of bone resorption inducers.

Material and Methods.

Bone resorption was determined by quantification of calcium release from neonatal mouse calvaria (skull bones) in a tissue culture system, into supernatant medium. Calvaria were prepared from 4 days old mice (body weight 4–4.5 g) of time controlled mated Swiss albino mice. Frontal and parietal calvarial parts were dissected under a stereomicroscope and halved along the median suture. Half calvaria from all animals were randomly distributed to 6-well culture dishes (NUNC), containing stainless steel grids to support the bones at the interface of gas and medium. The tissue is incubated in BGJ medium (Bioconcept, Switzerland) according to a specified formulation supplemented with 1 mg/ml BSA (bovine serum albumin, SIGMA). Calvaria were cultured at 37° C. in humidified atmosphere of 5% $CO_2$ and 95% air. After 24 hours of preincubation, they were transferred to new dishes containing 1.7 ml fresh medium and test substances. Bone resorption inducers and retinoid antagonists were tested either as single agents or in combination. The cultures were then run for 72 hours.

Calcium concentrations in culture supernatants were measured immediately after each incubation period. Stable, free calcium was determined in 25 μl samples with a spectrophotometric method using a methylthymol blue containing kit (Biomérieux), (E. M. Gindler and J. D. King, Am. J. Clin. Pathol. 1972, 58, 376–382). The resorptive response was expressed as μg calcium released per half calvarium during 3 days treatment.

Additional tests were done to examine calcium remaining in the calvaria. Calcium was extracted with 5% trichloroacetic acid (TCA) and determined in 50 μl samples after neutralization with NaOH. Furthermore, bone tissue viability was determined to exclude cytotoxicity. This was quantified by the colorimetric MTT tetrazolium test (T. Mosmann, J. Immunol. Methods 1983, 65, 55–63).

In these test, retinoid antagonists H and B were used.

The following bone resorption inducing/stimulating agents were used:

Calcitriol (1,25-dihydroxyvitamin $D_3$), all-trans retinoic acid (all-trans RA), and 9-cis retinoic acid (9-cis RA), were synthesized by Roche Laboratories Basel.

Prostaglandin E2 (PGE2), cell culture tested (Sigma Chem. Co.),

Tumor necrosis factor a (TNFa), murine recombinant, and Interleukin-1α (IL-1α), murine recombinant (Calbiochem.).

Bone resorption induced by the various agents was determined by measuring the amount of calcium released from half calvaria into the supernatant medium. Calcium release is indicated in μg per half calvarium in 1.7 ml medium. Calcium release from calvaria into medium as well as uptake of calcium from medium into calvaria can be measured. Efficacy of retinoid antagonists to inhibit the activity of bone resorption inducers is expressed as % inhibition. It is calculated from the difference between the amount of released calcium by bone resorption inducers alone and the amount of released calcium by their combination with retinoid antagonists. Retinoid antagonists alone induce neither calcium release nor uptake. Basal resorption rate in vehicle controls was 5 or less than 5%.

Results.

The results of the experiments (tables 6 to 11) demonstrate that retinoid antagonists H and B counteract bone resorption induced by six different agents. These latter are considered to contribute to bone resorption responsible for osteoporosis and bone fractures in mammals and human beings. As can be seen from tables 6 to 11, all six bone resorbing agents induced a dose dependent calcium release from calvaria bone into the supernatant medium. Retinoid antagonists were able to inhibit calcium release induced by these six different bone resorbing agents.

TABLE 6

Inhibition of bone resorption by retinoid antagonists
Calcitriol as inducing agent

| Bone resorption inducer | Retinoid antagonist | | Calcium release per half calvarium | | Inhibition of bone resorption by retinoid antagonists | |
|---|---|---|---|---|---|---|
| Calcitriol | H | B | (μg) | | (%) | |
| (nM) | (μM) | (μM) | H | B | H | B |
| 3 | — | — | 13 ± 3 | | — | — |
| 1 | — | — | 9 ± 4 | | — | — |
| 0.3 | — | — | 4 ± 3 | | — | — |
| 3 | 1 | — | 11 ± 6 | | 15.4 | — |
| 1 | 1 | — | 4 ± 3 | | 55.6 | — |
| 0.3 | 1 | — | 0 ± 3 | | 100 | — |
| 3 | — | 1 | | 4 ± 4 | — | 69.2 |
| 1 | — | 1 | | 5 ± 3 | — | 44.4 |
| 0.3 | — | 1 | | −1 ± 2 | — | 125 |

TABLE 7

All-trans Retinoic Acid as inducing agent

| Bone resorption inducer | Retinoid antagonist | | Calcium release per half calvarium | | Inhibition of bone resorption by retinoid antagonists | |
|---|---|---|---|---|---|---|
| all-trans RA | H | B | (μg) | | (%) | |
| (μM) | (μM) | (μM) | H | B | H | B |
| 1 | — | — | 23 ± 8 | 17 ± 3 | — | — |
| 0.1 | — | — | 19 ± 11 | 13 ± 3 | — | — |
| 0.01 | — | — | 1 ± 4 | 1 ± 2 | — | — |
| 1 | 10 | — | −2 ± 3 | | 108.7 | |
| 0.1 | 10 | — | −5 ± 4 | | 126.3 | |
| 0.1 | 1 | — | 2 ± 11 | | 89.5 | |
| 1 | — | 10 | | 10 ± 7 | | 41.2 |
| 0.1 | — | 10 | | −3 ± 4 | | 123.1 |
| 0.1 | — | 1 | | 5 ± 4 | | 61.5 |

TABLE 8

9-cis Retinoic Acid as inducing agent

| Bone resorption inducer | Retinoid antagonist | | Calcium release per half calvarium | | Inhibition of bone resorption by retinoid antagonists | |
|---|---|---|---|---|---|---|
| 9-cis RA | H | B | (μg) | | (%) | |
| (μM) | (μM) | (μM) | H | B | H | B |
| 1 | — | — | 40 ± 11 | 18 ± 4 | — | — |
| 0.1 | — | — | 22 ± 8 | 17 ± 10 | — | — |
| 0.01 | — | — | 6 ± 10 | 3 ± 3 | — | — |
| 1 | 10 | — | 28 ± 7 | | 30 | |

TABLE 8-continued 9-cis Retinoic Acid as inducing agent

| Bone resorption inducer | Retinoid antagonist | | Calcium release per half calvarium | | Inhibition of bone resorption by retinoid antagonists | |
|---|---|---|---|---|---|---|
| 9-cis RA | H | B | (µg) | | (%) | |
| (µM) | (µM) | (µM) | H | B | H | B |
| 0.1 | 10 | — | −5 ± 3 | | 123 | |
| 0.1 | 1 | — | 4 ± 5 | | 82 | |
| 1 | — | 10 | | −6 ± 2 | | 133.3 |
| 0.1 | — | 10 | | −4 ± 3 | | 123.5 |
| 0.1 | — | 1 | | 2 ± 5 | | 33.3 |

TABLE 9

Prostaglandin E2 (PGE2) as inducing agent

| Bone resorption inducer | Retinoid antagonist | | Calcium release per half calvarium | | Inhibition of bone resorption by retinoid antagonists | |
|---|---|---|---|---|---|---|
| PGE2 | H | B | (µg) | | (%) | |
| (µM) | (µM) | (µM) | H | B | H | B |
| 1 | — | — | 18 ± 5 | | — | — |
| 0.3 | — | — | 12 ± 4 | | — | — |
| 0.1 | — | — | 9 ± 5 | | — | — |
| 1 | 1 | — | 16 ± 4 | — | 11.1 | — |
| 0.3 | 1 | — | 8 ± 2 | — | 33.3 | — |
| 0.1 | 1 | — | 9 ± 8 | — | 0 | — |
| 1 | — | 1 | — | 15 ± 2 | — | 16.7 |
| 0.3 | — | 1 | — | 7 ± 4 | — | 41.7 |
| 0.1 | — | 1 | — | 2 ± 3 | — | 77.8 |

TABLE 10

Tumor Necrosis Factor α (TNF-α) as inducing agent

| Bone resorption inducer | Retinoid antagonist | | Calcium release per half calvarium | | Inhibition of bone resorption by retinoid antagonists | |
|---|---|---|---|---|---|---|
| TNF-α | H | B | (µg) | | (%) | |
| (ng/ml) | (µM) | (µM) | H | B | H | B |
| 100 | — | — | 24 ± 3 | | — | — |
| 30 | — | — | 18 ± 8 | | — | — |
| 10 | — | — | 3 ± 4 | | — | — |
| 100 | 1 | — | 20 ± 4 | | 16.7 | |
| 30 | 1 | — | 20 ± 4 | | −11.1 | |
| 10 | 1 | — | 7 ± 6 | | −133.3 | |
| 100 | — | 1 | | 17 ± 3 | | 29.2 |
| 30 | — | 1 | | 12 ± 9 | | 33.3 |
| 10 | — | 1 | | 3 ± 4 | | 0 |

TABLE 11

Interleukin 1α (IL-1α) as inducing agent

| Bone resorption inducer | Retinoid antagonist | | Calcium release per half calvarium | | Inhibition of bone resorption by retinoid antagonists | |
|---|---|---|---|---|---|---|
| IL-1α | H | B | (µg) | | (%) | |
| (nM) | (µM) | (µM) | H | B | H | B |
| 0.1 | — | — | 38 ± 5 | | — | — |
| 0.01 | — | — | 31 ± 9 | | — | — |
| 0.001 | — | — | 31 ± 10 | | — | — |
| 0.1 | 1 | — | 25 ± 6 | | 34.2 | |

TABLE 11-continued

Interleukin 1α (IL-1α) as inducing agent

| Bone resorption inducer | Retinoid antagonist | | Calcium release per half calvarium | | Inhibition of bone resorption by retinoid antagonists | |
|---|---|---|---|---|---|---|
| IL-1α | H | B | (μg) | | (%) | |
| (nM) | (μM) | (μM) | H | B | H | B |
| 0.01 | 1 | — | 24 ± 10 | | 19.4 | |
| 0.001 | 1 | — | 8 ± 9 | | 27.3 | |
| 0.1 | — | 1 | | 28 ± 8 | | 26.3 |
| 0.01 | — | 1 | | 26 ± 5 | | 16.1 |
| 0.001 | — | 1 | | 12 ± 6 | | −9.1 |

EXAMPLE 8

Efficacy of topical application of Compound B in the treatment of precancerous lesions of the skin (multiple actinic keratoses)

In a clinical trial, a cream containing 1% of Compound B was applied on the lesions twice daily without occlusive dressing. The results are given in Table 12. As can be seen from Table 12, Compound B when administered topically is effective in the therapy of precancerous lesions of the skin and is - in contrast to other retinoids- well tolerated without inducing any irritation of the lesions and the surrounding skin.

TABLE 12

| Patient | Sex | Age (Years) | Localisation | Duration of Therapy | Reduction in Size of Lesions | Improvement | Adverse Events* |
|---|---|---|---|---|---|---|---|
| I | m | 53 | both forearms | 4 months | 50% | marked | none |
| II | m | 61 | face | 6 weeks | 20% | slight | none |
| III | f | 69 | face | 4 months | 30% | moderate | none |
| IV | m | 75 | face and back of both hands | 3 months | 30% | moderate | none |
| V | m | 74 | face | 2 months | 0% | no | none |

*particularly irritation of lesions and surrounding skin

In accordance with the present invention the compounds of formula I can be prepared by reacting a compound of formula XVIII

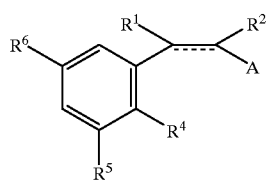

XVIII with a compound of formula XIX

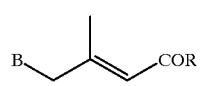

XIX wherein A is formyl and B is di-(lower alkoxy)phosphinyl; R is lower alkoxy; and $R^1$, $R^2$ and $R^4$ to $R^6$ are as defined above;
to yield a compound of formula I wherein $R^3$ is lower alkoxy, and, if desired, hydrolysing the lower alkoxy group $R^3$ in the so obtained compound of formula I.

The reaction of the compound XVIII with the compound XIX can be carried out according to methods which are known per se for the Horner (Wadsworth-Emmons) reaction. The reaction can be carried out in the presence of a base and, preferably, in the presence of an inert organic solvent, e.g. in the presence of sodium hydride in benzene, toluene, dimethylformamide, tetrahydrofuran, dioxane or a 1,2-dimethoxyalkane, or also a sodium alcoholate in an alkanol, e.g. sodium methylate in methanol, in a temperature range lying between 0° and the boiling point of the reaction mixture. Another example for a base which can be used in that reaction is lithium bis(trimethylsilyl)amide in an inert solvent like THF in a temperature range between −78° C. and 0° C. A thus-obtained carboxylic acid ester of formula I can be hydrolyzed in a manner known per se, e.g. by treatment with alkalis, especially by treatment with aqueous-alcoholic sodium or potassium hydroxide solution in a temperature range lying between room temperature and the boiling point of the reaction mixture.

The thus-obtained carboxylic acid of formula I can be isolated in a manner known per se as such or as a salt, e.g. as an alkali salt, especially as the Na or K salt.

The compounds of formula XVIII are novel compounds and are also an object of the present invention. The compounds of formula XVIII can be prepared as set forth in Schemes 1 and 2 below:

Scheme 1

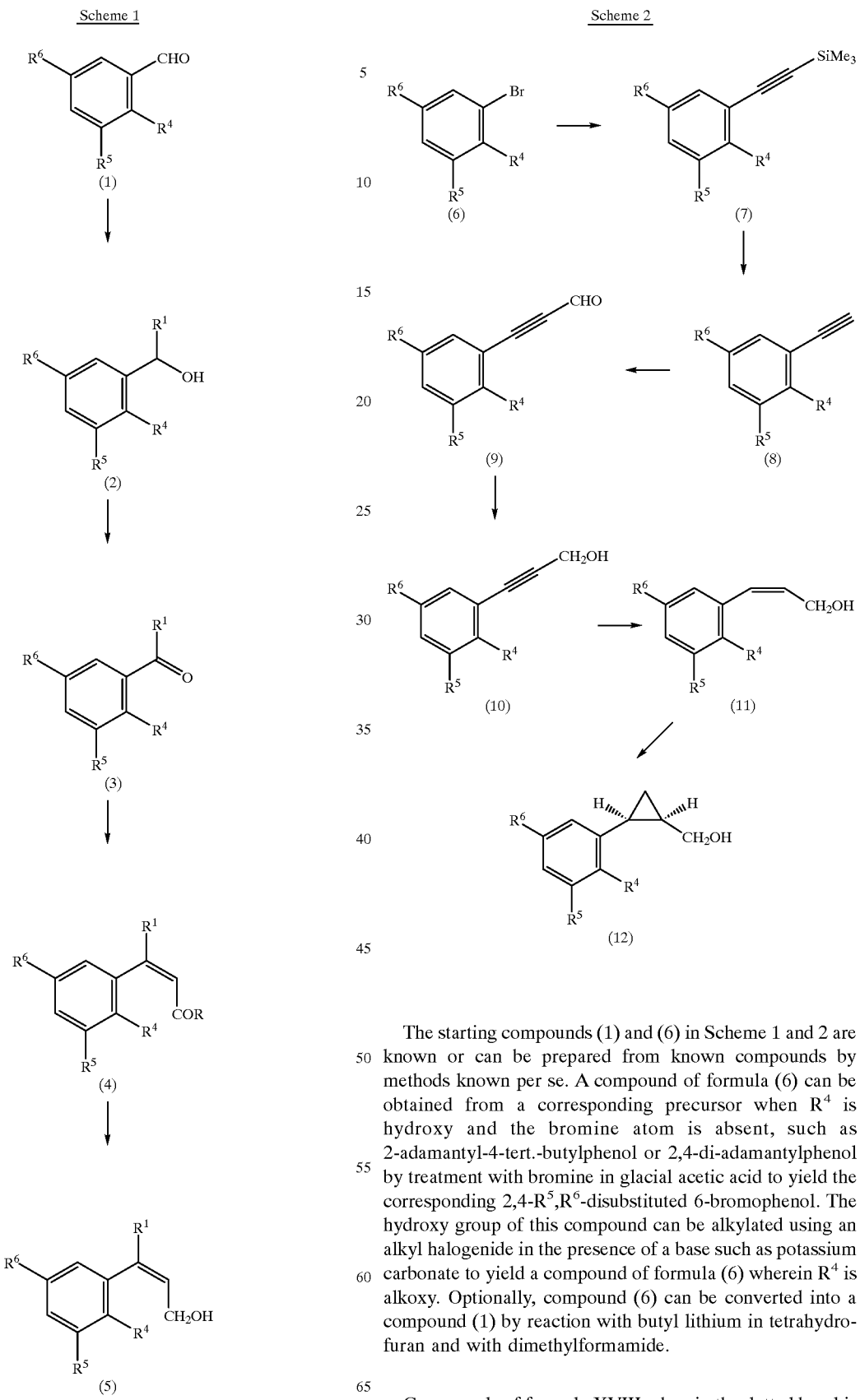

Scheme 2

The starting compounds (1) and (6) in Scheme 1 and 2 are known or can be prepared from known compounds by methods known per se. A compound of formula (6) can be obtained from a corresponding precursor when $R^4$ is hydroxy and the bromine atom is absent, such as 2-adamantyl-4-tert.-butylphenol or 2,4-di-adamantylphenol by treatment with bromine in glacial acetic acid to yield the corresponding 2,4-$R^5$,$R^6$-disubstituted 6-bromophenol. The hydroxy group of this compound can be alkylated using an alkyl halogenide in the presence of a base such as potassium carbonate to yield a compound of formula (6) wherein $R^4$ is alkoxy. Optionally, compound (6) can be converted into a compound (1) by reaction with butyl lithium in tetrahydrofuran and with dimethylformamide.

Compounds of formula XVIII wherein the dotted bond is present, $R_1$ is lower alkyl and $R^2$ is hydrogen can be obtained according to Scheme 1. In Scheme 1, compound (1) is converted to compound (2) by reaction with an organometallic nucleophile like an alkyl lithium or alkyl magnesium halogenide. Compound (2) can be oxidized to form compound (3) by treatment with oxidizing agents such as manganese dioxide. Compound (3) can be converted to compound (4) in a Peterson olefination [Synthesis, 384 (1984) D. J. Ager, J. Org. Chem. 33, 780 (1968) D. J. Peterson] by reaction with ethyl trimethylsilyl acetate. The carboxylic ester group in compound (4) can be reduced to a hydroxy methyl group by treatment with a metal hydride such as diisobutyl aluminum hydride to give compound (5) which can be oxidized by treatment with oxidizing agents such as manganese dioxide to give a compound of formula XVIII wherein $R^1$ is lower alkyl and $R^2$ is hydrogen.

Compounds of formula XVIII wherein the dotted bond is absent and $R^1$ and $R^2$ taken together are methylene can be obtained as set forth in Scheme 2. According to Scheme 2, compound (6) is reacted with trimethylsilyl acetylene in the presence of tetrakis (triphenyl-phosphine) palladium(0) and CuI to yield compound (7) which, after removal of the trimethylsilyl group by treatment with tetrabutyl ammonium fluoride and formylation of the so-obtained compound (8) with dimethyl formamide in the presence of a base such as butyl lithium yields compound (9). The formyl group in compound (9) can be reduced to the hydroxymethyl group by treatment with a metal hydride such as sodium borohydride in ethanol to give compound (10). Reduction of the triple bond in compound (10) e.g., by means of a Lindlar catalyst, affords compound (11) which is converted to compound (12) by a modified Simmons-Smith reaction [Tetrahedron 24, 53 (1968) J. Furukawa, N. Kawabata, J. Nishimura, J. Org. Chem. 42, 3031 (1977) N. Kawabata et al.]. This cyclopropanation can also be carried out in an enantioselective way according to the method of Fujisawa et al. (Chem. Letters, 61 (1992) using (R,R) or (S,S)-diethyltartrate as chiral auxiliary. Compound (12) can be oxidized using methods known in the art, e.g., by pyridinium chlorochromate, or by a Swern- or Dess-Martin oxidation to yield a compound of formula XVIII wherein A is formyl, the dotted bond is absent and $R_1$ and $R^2$ taken together are methylene.

All these reactions can be carried out in a manner known per se.

The invention is illustrated further by the EXAMPLEs which follow.

EXAMPLE 9

4.0 g of 3,5-di-tert.-butyl-2-hydroxybenzaldehyde (CAS # 37942-07-7) was dissolved in dimethylformamide (DMF). This was treated with 0.89 g of sodium hydride (50% in oil suspension) and stirred at 25° C. until hydrogen was no longer evolved. To this was added 2.01 ml n-bromobutane and the mixture was heated to 85° C. for 14 hr. This was cooled and poured into water. The aqueous was extracted with ether. The ether layer was washed with water, dried ($MgSO_4$), and solvent was removed. Purification was accomplished by florsil column chromatography (15% ether/hexane) to give 5.4 g of 3,5-di-tert.-butyl-2-butyloxybenzaldehyde; $^1H$ NMR ($CDCl_3$) δ 10.31 (s, 1H,aldehyde), 7.70 (dd,4H,aromatics), 3.94 (t,2H,—$OCH_2$—).

3.5 g of 3,5-di-tert.-butyl-2-butyloxybenzaldehyde was dissolved in 30 ml of ethyl ether and cooled with stirring to 0° C. 11.4 ml of methyl lithium (1.55M in ether) was added via syringe. This was stirred for 10 min. and poured into 1M ammonium chloride and shaken. The ether layer was separated, dried ($Na_2SO_4$), and solvent removed to give 3.7 g of an oil which was purified by chromatography (silica gel –5% etherlhexane) to give 3.3 g of 1-(3,5-di-tert.-butyl-2-butyloxyphenyl)ethanol; $^1H$ NMR ($CDCl_3$) δ 7.34 (dd,4H, aromatics), 5.25 (m,1H,—$CH_3C\underline{H}$—), 3.85 (t,2H,—$OCH_2$—).

2.77 g (9 mmol) of 1-(3,5-di-tert.-butyl-2-butyloxyphenyl)ethanol was dissolved in 120 ml of toluene that had been treated with 14 g of manganese(IV)oxide. This was well stirred at 75° C. for 5 hr. This was cooled and filtered through celite. Solvent was removed to give 2.27 g of 1-(3,5-di-tert.-butyl-2-butyloxyphenyl)ethanone. $^1H$ NMR ($CDCl_3$) δ 7.38 (dd,4H,aromatics), 2.62 (s,3H, C $\underline{H}_3C$—), 3.72 (t, 2H, —$OCH_2$—).

1.43 g of diisopropylamine in 20 ml of tetrahydrofuran (THF) was treated with 8.4 ml of n-butyl lithium (1.6M in hexane) at –20° C. This was cooled to –78° C. and treated with 2.26 g ethyl trimethylsilylacetate. This was allowed to warm to 0° C. and poured into water and extracted into hexane. The extract was washed with water, dried ($MgSO_4$), and had solvent removed to give an oil. Purification and separation of isomers was accomplished by silica gel chromatography (15% etherlhexane) to give 3.5 of (Z)-3-(3,5-di-tert.-butyl-2-butyloxyphenyl)-butenoic acid ethyl ester. $^1H$ NMR ($CDCl_3$) δ 7.05 (dd, 4H, aromatics), 5.90 (s, 1H, 2-H), 3.96 (q, 2H, —$OCH_2CH_3$), 3.70 (t, 2H, —$OCH_2$—), 2.21 (s, 3H).

0.9 g of (E)-3-(3,5-di-tert.-butyl-2-butyloxyphenyl)-butenoic acid ethyl ester was dissolved in 20 ml of dry ether. This was cooled to –78° C. and treated with 6.0 ml of diisobutylaluminum hydride (1.0M in hexane). The temperature was allowed to warm to 0° C. and was then treated with 20% aqueous Rochelle salt. This was stirred at 25° C. for 1 hr. The organic fraction was separated, washed with water, dried ($Na_2SO_4$), and had solvent removed to give 0.78 g of (Z)-3-(3,5-di-tert.-butyl-2-butyloxyphenyl)-buten-1-ol. $^1H$ NMR ($CDCl_3$) δ 7.08 (dd, 4H, aromatics), 5.90 (t, 1H, C $\underline{H}$—OH), 3.80 (t, 2H, —$OCH_2$—), 2.49 (t, 1H, —$O\underline{H}$), 2.21 (s, 3H).

0.66 g of (Z)-3-(3,5-di-tert.-butyl-2-butyloxyphenyl)-buten-1-ol was dissolved in 100 ml ether and cooled to 15° C. 6.6 g of manganese(IV)oxide slurried in 50 ml ether was added to the above solution. This was stirred at ambient for 3 hr. The mixture was filtered through celite and had the solvent removed. This gave 0.64 g of (Z)-3-(3,5-di-tert.-butyl-2-butyloxyphenyl)-buten-1-al. $^1H$ NMR ($CDCl_3$) δ 9.45 (d, 1H, aldehyde), 7.08 (dd, 4H, aromatics), 5.90 (t, 1H, C$\underline{H}$—OH), 3.80 (t, 2H,—$OC\underline{H}_2$—), 2.49 (t, 1H, —$O\underline{H}$), 2.21 (s, 3H). 635 mg of triethyl-3-methyl-4-phosphonocrotonate (CAS # 41891-54-7) was dissolved in 5 ml THF, cooled to –78° C. and treated with 2.2 ml (2.2 mmol) (1.0M in THF) of lithium bis(trimethylsilyl)amide. While at –78° C., 600 mg of (Z)-3-(3,5-di-tert.-butyl-2-butyloxy-phenyl)-buten-1-al in 5 ml THF was slowly added. This was stirred at –78° C. for 0.5 hr. and poured into dilute aqueous ammonium chloride. The product was extracted into hexane and the organic portion washed with water, dried ($Na_2SO_4$), and had the solvent removed to give a crude oil. Purification and isomer separation was accomplished by silica gel chromatography (3% ether/hexane) to give 540 mg of (2E,4E,6Z)-7-(3,5-di-tert.-butyl-2-butyloxyphenyl)-3,7-dimethyl-2,4,6-heptatrienoic acid ethyl ester.

$^1H$ NMR ($CDCl_3$) δ 7.12 (dd, 4H, aromatics), 6.62 (dd, 1H, H-5), 6.20 (d, 1H,H-4), 6.18 (d, 1H,H-6), 4.15 (q, 3H, —$OCH_2$ $C\underline{H}_3$), 3.7 (dt, 2H, —$OCH_2$—), 2.22 (s, 3H), 2.15 (s, 3H).

520 mg of (2E,4E,6Z)-7-(3,5-di-tert.-butyl-2-butyloxyphenyl)-3,7-dimethyl-2,4,6-heptatrienoic acid ethyl ester was suspended in 5 ml ethanol and treated with 5 ml 6N NaOH and refluxed for 1.5 hr. This was cooled and acidified to pH 3 with dilute HCl. The solid which precipitated was extracted into chloroform. The organic portion was washed with water, dried ($Na_2SO_4$), and had the solvent removed. This gave a solid which was crystallized from methylene chloride/hexane to give (2E,4E,6Z)-7-[3,5-di-tert.butyl-2-butyloxyphenyl]-3-methyl-2,4,6-octatrienoic acid. $^1$H NMR ($CDCl_3$) δ 7.08 (dd, 4H, aromatics), 6.65 (dd, 1H,H-5), 6.22 (d, 1H,H-4), 6.18 (d, 1H,H-6), 3.7 (dt, 2H, —$OCH_2$—), 2.24 (s, 3H), 2.15 (s, 3H). M.p. 148–151° C.

In analogy to the above procedure the following compounds were prepared:

(2E,4E,6Z)-7-[3,5-di-tert.butyl-2-methoxyphenyl]-3-methyl-2,4,6-octatrienoic acid, m.p. 208–211° C. (from THF/hexane)

(2E,4E,6Z)-7-[3,5-di-tert.butyl-2-ethoxyphenyl]-3-methyl-2,4,6-octatrienoic acid, m.p. 165–167° C. (from THF/hexane)

(2E,4E,6Z)-7-[3,5-di-tert.butyl-2-hexyloxyphenyl]-3-methyl-2,4,6-octatrienoic acid, m.p. 156–160° C. (from ether/hexane)

(2E,4E,6Z)-7-[3,5-di-tert.butyl-2-octyloxyphenyl]-3-methyl-2,4,6-octatrienoic acid, m.p. 137–139° C. (from hexane).

EXAMPLE 10

A solution of 13 g of 2-bromo-4,6-di-tert.butyl-phenol in 100 ml of dimethylformamide (DMF) was added dropwise to a suspension of 2.2 g of sodium hydride (50% in mineral oil) in 100 ml of DMF at 0° C. The reaction mixture was stirred at room temperature until hydrogen was no longer evolved (ca. 1 h), cooled again to 0° C. and treated with a solution of 22 g of ethyl iodide in 50 ml of DMF. After stirring for about 1 hour at room temperature, the reaction mixture was poured on icewater, extracted with ethyl acetate, washed ($H_2O$), dried ($Na_2SO_4$) and evaporated to give 13.5 g of 1-bromo-2-ethoxy-3,5-di-tert.butyl-benzene as white crystals, m.p. 55–56° C.

10.1 g of 1-bromo-2-ethoxy-3,5-di-tert.butyl-benzene were dissolved in 50 ml of piperidine. After the addition of 490 mg of tetrakis(triphenylphosphine)palladium(0), 96 mg of copper(I)iodide and 140 mg of triphenylphosphine, the reaction mixture was heated to 90° C. under argon and slowly treated with 6.3 g of (trimethylsilyl)acetylene (ca. 2 hours). The reaction was kept for further 10 minutes at 90° C. before this procedure was repeated using the same amount of reagents. The reaction mixture was heated for another hour to 90° C., then poured on icewater, acidified with 80 ml of concentrated hydrochloric acid, extracted with ethyl acetate, washed ($H_2O$), dried ($Na_2SO_4$) and evaporated. The resulting oil was purified by chromatography (silica gel, hexane/2.5% ethyl acetate) to give 8.3 g of 3,5-di-tert.butyl-2-ethoxy-phenylethynyl)-trimethylsilane as a slightly yellow oil.

8.3 g of this oil were dissolved in 120 ml of tetrahydrofuran (THF) and treated with 6.03 g of tetrabutylarnmonium fluoride. After 1 hour of stirring at ambient temperature, the reaction mixture was poured on icewater, extracted with ether, washed ($H_2O$), dried ($Na_2SO_4$) and evaporated. Purification of the resulting brown oil by chromatography (silica gel, hexane) gave 4.2 g of 1,5-di-tert.butyl-2-ethoxy-3-ethynyl-benzene as colourless oil which crystallized in the refrigerator, m.p. 46–47° C. A small sample was sublimed in high vacuum and melted at 48–49° C.

4.1 g of this compound were dissolved in 45 ml of THF and treated with 11 ml of n-BuLi (1.6 molar in hexane) at −78° C. After 1 hour at −78° C. the reaction mixture was treated with 12 ml of DMF, warmed to room temperature, stirred for 6 hours, poured on icewater, acidified with concentrated hydrochloric acid, extracted with ethyl acetate, washed ($H_2O$), dried ($Na_2SO_4$) and evaporated to give 5 g of a brown oil which was purified by chromatography (silica gel, hexane/2% ether). The combined pure fractions yielded 2.4 g of Et slightly orange oil, which crystallized in the freezer, m.p. 55–57° C.

2.4 g of 3,5-di-tertbutyl-2-ethoxy-phenyl)-propynal were dissolved in 25 ml of ethanol and treated with 90 mg of sodium borohydride during 1.5 hours at 0° C. The reaction mixture was acidified with 6 ml of 2N hydrochloric acid, poured on icewater, extracted with ether, washed ($H_2O$), dried ($Na_2SO_4$) and evaporated. The resulting orange oil was purified by chromatography (silica gel, hexane:ethyl acetate=9:1) and recrystallized from pentane to give 2.2 g of 3-(3,5-di-tert.butyl-2-ethoxy-phenyl)-prop-2-yn-1-ol as white crystals, m.p. 82–84° C.

2 g of this compound were dissolved in 350 ml of ethanol, treated with 100 mg of Lindlar-catalyst and hydrogenated at normal pressure for 7.5 hours. After 3,5 and 6 hours, 100 mg each of fresh Lindlar-catalyst were added. The catalyst was filtered off and the reaction solution evaporated. The resulting residue was purified by medium pressure chromatography (silica gel, hexane:ether=8:2) and gave after crystallisation from hexane 1.3 g of (Z)-3-(3,5-di-tert.butyl-2-ethoxy-phenyl)-prop-2-en-1-ol, mp. 93–94° C.

1.3 g of this compound were dissolved in 50 ml of methylene chloride and treated with 13.7 ml of diethylzinc (1M in hexane) at −5° C. After 15 minutes of stirring at 0° C., the reaction mixture was cooled to −20° C., treated dropwise with 7.4 g of methylene iodide, stirred for 1 hour at 0° C. and 1.5 hours at room temperature and recooled to 0° C. 50 ml of saturated, aqueous ammonium chloride were dropped slowly into the white suspension. The clear reaction mixture was poured onto ice/saturated ammonium chloride solution, extracted with ether, washed ($H_2O$), dried ($Na_2SO_4$) and evaporated. The semi-crystalline residue was chromatographed (silica gel, hexane:ethyl acetate=9:1) and gave after recrystallisation from hexane 1.3 g of (1RS,2SR)-[2-(3,5-di-tert.butyl-2-ethoxy-phenyl)-cyclopropyl]-methanol as white crystals, m.p. 102–103° C.

1.02 g of oxalyl chloride were dissolved in 37 ml of $CH_2Cl_2$ and treated with 0.86 ml of dimethyl sulfoxide at −60° C. After shortly warming to −35° C., the reaction mixture was recooled to −60° C. and treated with a solution of 1.2 g of (1RS,2SR)-[2-(3,5-di-tert.butyl-2-ethoxy-phenyl)-cyclopropyl]-methanol in 20 ml of $CH_2Cl_2$. After 15 minutes of stirring at −50° C., 1.7 ml of triethylamine were dropped in. The reaction mixture was stirred for 2 hours at room temperature, poured on icewater, extracted with ether, washed ($H_2O$), dried ($Na_2SO_4$) and evaporated. The crude material was purified by flash chromatography (silica gel, hexane:ethyl acetate=9:1) and recrystallized from hexane to give 1.01 g of (1RS,2RS)-2-(3,5- di-tert.butyl-2-ethoxy-phenyl)-cyclopropanecarbaldehyde as white crystals, m.p. 96–97° C.

908 mg of triethyl 3-methyl-4-phosphonocrotonate were dissolved in 25 ml of THF and treated with 3.4 ml of lithium bis(trimethylsilyl)amide (1.0 molar in THF) at −78° C. After 0.5 hour, a solution of 800 mg of the above described aldehyde in 25 ml of THF was slowly added. The cooling bath was removed and the temperature allowed to warm to 0° C. After 1.5 hours at 0° C., the reaction mixture was poured on saturated, aqueous ammonium chloride, extracted with ether, washed (H$_2$O), dried (Na$_2$SO$_4$) and evaporated. The crude product was purified by flash chromatography (silica gel, hexane:ethyl acetate=9:1) and medium pressure chromatography (silica gel, hexane/2% ethyl acetate) to give after recrystallisation from hexane/ethyl acetate 650 mg of (2E,4E)-(1RS,2RS)-5-[2-(3,5-di-tert.butyl-2-ethoxy-phenyl)-cyclopropyl]-3-methyl-penta-2,4-dienoic acid ethyl ester as white crystals, m.p. 129–130° C. and 370 mg of (2Z,4E)-(1RS,2RS)-5-12-(3,5-di-tertwbutyl-2-ethoxy-phenyl)-cyclopropyl]-3-methyl-penta-2,4-dienoic acid ethyl ester, m.p. 123–126° C.

600 mg of the (2E,4E)-ester were dissolved in 20 ml of ethanol and treated with a solution of 840 mg of potassium hydroxide in 4 ml each of ethanol and water. After the addition of 10 ml of THF, the clear solution was warmed to 45–50° C. for 7 hours, cooled to room temperature, poured in ice/1N hydrochloric acid, extracted with ethyl acetate, washed (H$_2$O), dried (Na$_2$SO$_4$) and evaporated. The crude material was recrystallized from ethyl acetate to give 440 mg of (2E,4E)-(1RS,2RS)-5-[2-(3,5-di-tert butyl-2-ethoxy-phenyl)-cyclo-propyl]- 3-methyl-penta-2,4-dienoic acid as white crystals, m.p. 200–202° C. According to the same procedure 370 mg of the (2Z,4E)-ester were hydrolized to give 270 mg of (2Z,4E)-(1RS,2RS)-5-[2-(3,5-di-tert.butyl-2-ethoxy-phenyl)-cyclopropyl]-3-methyl-penta-2,4-dienoic acid, m.p. 169–174° C.

EXAMPLE 11

In analogy to Example 2, (2E,4E)-(1RS,2RS)-5-[2-(3,5-di-tert.butyl-2-butoxy-phenyl)-cyclopropyl]-3-methyl-penta-2,4-dienoic acid, m.p. 175–178° C. (hexane/ethyl acetate) was synthesized using 1-bromo-2-butoxy-3,5-di-tert.butyl-benzene as starting material. The following Examples describe pharmaceutical formulations according to the invention:

EXAMPLE 12

| a) Fill mass for soft gelatin capsules | |
|---|---|
| Active compound | 5.0–200.0 g |
| Oil* | 1–3 parts |
| Wax mixture** | 1–5 parts |
| Fill volume | 1–6 minims |

| b) 20 mg Soft Gelatin Capsules | |
|---|---|
| Ingredients | mg/capsule |
| Active compound | 20.000 |
| dl-α-Tocopherol | 0.028 |
| Hydrogenated Castor Oil | 4.200 |
| Caprylic/Capric/Stearic Triglyceride (Synthetic Triglyceride) | 56.000 |
| Triglyceride, Medium Chain | 199.772 |
| Total | 280.000 mg |

*natural vegetable oils, e.g. soy oil, peanut oil, and artificial glycerides
**composition of natural and artificial waxes or partially hydrogenated fats

EXAMPLE 13

| Hard Gelatine capsules containing 20 mg active substance: One Capsule contains: | |
|---|---|
| Active compound | 20.0 mg |
| Gelatine Bloom 30 | 70.0 mg |
| Maltodextrin MD 05 | 108.0 mg |
| dl-α-Tocopherol | 2.0 mg |
| Sodium ascorbate | 10.0 mg |
| Microcrystalline cellulose | 48.0 mg |
| Magnesium stearate | 2.0 mg |
| (weight capsule content) | 260.0 mg |

Procedure:

The active substance is wet milled in a solution of gelatine, maltodextrin, dl-□-Tocopherol and sodium ascorbate.

The wet milled suspension is spray-dried.

The spray-dried powder is mixed with microcrystaline cellulose and magnesium stearate. 260 mg each of this mixture are filled into hard gelatine capsules of suitable size and color.

EXAMPLE 14

| Tablet containing 20 mg active substance: | |
|---|---|
| Tablet kernel: | |
| Active compound | 20.0 mg |
| Anhydrous lactose | 130.5 mg |
| Microcrystalline Cellulose | 80.0 mg |
| dl-α-Tocopherol | 2.0 mg |
| Sodium ascorbate | 10.0 mg |
| Polyvinylpyrrolidone K30 | 5.0 mg |
| Magnesium stearate | 2.5 mg |
| (Kernel weight) | 250.0 mg |
| Film coat: | |
| Hydroxypropyl methylcellulose | 3.5 mg |
| Polyethylenglycol 6000 | 0.8 mg |
| Talc | 1.3 mg |
| Irone oxide, yellow | 0.8 mg |
| Titanium dioxide | 0.8 mg |
| (weight of the film) | 7.4 mg |

Procedure:

The compound is mixed with anhydrous lactose and microcrystalline cellulose.

The mixture is granulated in water with a solution/dispersion of polyvinylpyrrolidone, dl-α-Tocopherol and sodium ascorbate.

The granular material is mixed with magnesium stearate and afterwards pressed as kernels with 250 mg weight.

The kernels are film coated with a solution/suspension of above-mentioned compositions.

EXAMPLE 15

| Sachet containing active substance | |
|---|---|
| Active compound | 200.0 mg |
| Lactose, fine powder | 990.0 mg |
| Microcrystalline Cellulose | 1250.0 mg |
| Sodium Carboxymethyl cellulose | 14.0 mg |
| dl-α-Tocopherol | 5.0 mg |
| Sodium ascorbate | 20.0 mg |
| Polyvinylpyrrolidone K30 | 10.0 mg |
| Magnesium stearate | 10.0 mg |

EXAMPLE 16

| Lotion (solution) | | preferred |
|---|---|---|
| Active compound | 0.1–2.0 g | |
| Propylene Glycol | 5.00–20.00 g | 10.00 g |
| PEG-Glyceryl Cocoate* | 0.00–20.00 g | 10.00 g |
| dl-α-Tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr.** | 0.00–0.20 g | 0.01 g |
| Isopropanol*** | 40.00–90.00 g | 50.00 g |
| Water, dem. ad | 100.00 g | 100.00 g resp. ml |

*or other tensides
**or other complexing agents e.g. EDTA
***or other alcohols e.g. Ethanol

Example 17

| Gel | | preferred |
|---|---|---|
| Active compound | 0.1–2.0 g | |
| Propylene Glycol | 5.00–20.00 g | 10.00 g |
| PEG-Glyceryl Cocoate* | 0.00–20.00 g | 10.00 g |
| dl-α-Tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr.** | 0.00–0.20 g | 0.01 g |
| Isopropanol*** | 40.00–90.00 g | 50.00 g |
| HPMC**** | 0.50–5.00 g | 3.00 g |
| Preservative***** | q.s. | q.s. |
| Water, dem. ad | 100.00 g | 100.00 g resp. ml |

*or other tensides
**or other complexing agents e.g. EDTA
***or other alcohols e.g. Ethanol
****Hydroxypropyl Methylcellulose or other polymers e.g. neutralised Carbomer, Methyl Cellulose, Sodium Carboxymethylcellulose
*****Preservatives e.g., Paraben esters (methyl, ethyl, propyl, butyl). Sorbic Acid. Benzoic Acid

EXAMPLE 18

| Cream | | preferred |
|---|---|---|
| Active compound | 0.1–2.0 g | |
| Glycerol | 0.00–10.00 g | 5.00 g |
| Na₂ EDTA | 0.001–0.50 g | 0.03 g |
| Glycerides* | 5.00–20.00 g | 10.00 g |
| Cetyl Alcohol | 0.50–5.00 g | 1.00 g |
| Stearyl Alcohol | 0.50–5.00 g | 1.00 g |
| Glycerol mono Stearate | 1.00–8.00 g | 4.00 g |
| Ceteareth** | 0.50–5.00 g | 2.00 g |
| dl-α-Tocopherol | 0.001–0.50 g | 0.02 g |
| Preservative*** | q.s. | q.s. |
| Water, dem. ad | 100.00 g | 100.00 g |

*e.g. Caprylic/Capric/Triglyceride, Caprylic/Capric/Linoleic Triglycerides, natural glycerides, as well as e.g. Propylene Glycol, Dicaprylate/Dicaprate and waxes, such as Stearyl, Stearate, Oleyl Oleate, Isopropyl Myristate
**Ceteareth 5–30, or other emulsifiers such as Polysorbase 20–80, Sorbitane esters of fatty acids, fatty acid esters of PEG.
***Preservatives e.g., Paraben esters (methyl, ethyl, propyl, butyl). Sorbic Acid. Benzoic Acid

EXAMPLE 19

| Aerosol for inhalation, metered dose inhaler | |
|---|---|
| Active compound | 0.5% (0.1–2.0%) |
| Sorbitantrioleate | 5% |
| dl-α-Tocopherol | 0.4% |
| Propellant (mixture of Trichlorofluoromethane and Dichlorodifluoromethane) | 94.1% |

EXAMPLE 20

| Dry powder inhaler | |
|---|---|
| Active compound (jet-milled, spray-dried) | 0.5 mg (0.1 mg–2.0 mg) |
| Lactose monohydrate | 25 mg |

What is claimed is:

1. A compound of the formula:

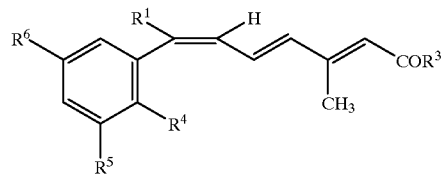

Ia wherein $R^1$ is lower alkyl; $R^3$ is hydroxy or lower alkoxy; $R^4$ is butoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule via a quaternary carbon atom;
or a pharmaceutically acceptable salt thereof.

2. The compound of claim 1, wherein $R^5$ and $R^6$ are $C_4$–$C_{12}$ alkyl.

3. The compound of claim 2, wherein the compound is (2E,4E,6Z)-7-[3,5-di-tert-butyl-2-butyloxyphenyl]-3-methyl-2,4,6-octatrienoic acid.

4. The compound of claim 2, wherein the compound is (2E,4E,6Z)-7-[3,5-di-tert-butyl-2-butyloxyphenyl]-3-methyl-2,4,6-octatrienoic acid ethyl ester.

5. A compound of the formula:

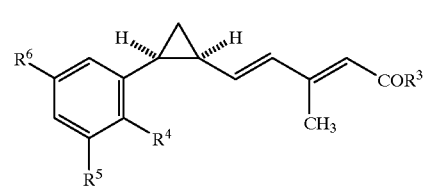

Ib wherein $R^3$ is hydroxy or lower alkoxy; $R^4$ is alkyl or alkoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule via a quaternary carbon atom;

or pharmaceutically acceptable salt thereof.

6. The compound of claim 5, wherein $R^5$ and $R^6$ are $C_4$–$C_{12}$ alkyl.

7. The compound of claim 6, wherein the compound is (2E,4E)-(1RS,2RS)-5-[2-(3,5-di-tert.butyl-2-ethoxy-phenyl)-cyclopropyl]-3-methyl-penta-2,4-dienoic acid ethyl ester.

8. The compound of claim 6, wherein said compound is (2E,4E)-(1RS,2RS)-5-[2-(3,5-di-tert.butyl-2-ethoxy-phenyl)-cyclopropyl]-3-methyl-penta-2,4-dienoic acid.

9. The compound of claim 6, wherein the compound is (2E,4E)-(1RS,2RS)-5-[2-(3,5-di-tert.butyl-2-butoxy-phenyl)-cyclopropyl]-3-methyl-penta-2,4-dienoic acid.

10. A compound of the formula:

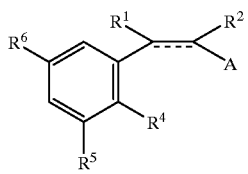

XVIII wherein A is formyl; the dotted bond can be either hydrogenated or form a double bond; and, when the dotted bond forms a double bond, $R^1$ is lower alkyl and $R^2$ is hydrogen; and, when the dotted bond is hydrogenated, $R^1$ and $R^2$ taken together are methylene to form a cis-substituted cyclopropyl ring; $R^3$ is hydroxy or lower alkoxy; $R^4$ is alkyl or alkoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule via a quaternary carbon atom.

11. A method for the treatment of osteoporosis, which comprises administering to a subject in need of such treatment an effective amount of (2E,4E)-(1RS,2RS)-5-[2-(3,5-di-tert-butyl-2-butoxy-phenyl)-cyclopropyl]-3-methyl-penta-2,4-dienoic acid.

12. A method for reducing or abolishing adverse events in a subject receiving retinoid agonist treatment, which comprises administering to such subject an effective amount of a retinoid antagonist of the formula:

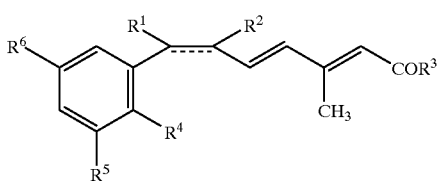

I wherein the dotted bond can be either hydrogenated or form a double bond, and, when the dotted bond forms a double bond, $R^1$ is lower alkyl and $R^2$ is hydrogen; and, when the dotted bond is hydrogenated, $R^1$ and $R^2$ taken together are methylene to form a cis-substituted cyclopropyl ring; $R^3$ is hydroxy or lower alkoxy; $R^4$ is alkyl or alkoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule via a quaternary carbon atom; or a pharmaceutically acceptable salt thereof.

13. A method for reducing or abolishing adverse events in a subject receiving retinoid agonist treatment, which comprises administering to such subject an effective amount of a retinoid antagonist of claim 1.

14. A method for reducing or abolishing adverse events in a subject receiving retinoid agonist treatment, which comprises administering to such subject an effective amount of a retinoid antagonist of the formula:

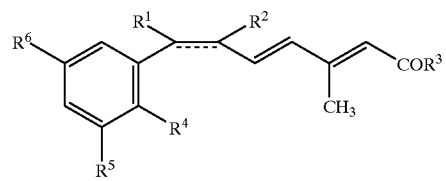

I wherein the dotted bond can be either hydrogenated or form a double bond, and, when the dotted bond forms a double bond, $R^1$ is lower alkyl and $R^2$ is hydrogen; and, when the dotted bond is hydrogenated, $R^1$ and $R^2$ taken together are methylene to form a cis-substituted cyclopropyl ring; $R^3$ is hydroxy or lower alkoxy; $R^4$ is alkyl or alkoxy; and $R^5$ and $R^6$ are, independently, a $C_{4-12}$ alkyl or a 5–12 cycloalkyl substituent containing from 1–3 rings which are either unsubstituted or substituted with from 1–3 lower alkyl groups, with the carbon atom of $R^5$ and $R^6$ being linked to the remainder of the molecule via a quaternary carbon atom; or a pharmaceutically acceptable salt thereof.

15. A method for reducing or abolishing adverse events in a subject receiving retinoid agonist treatment, which comprises administering to such subject an effective amount of a retinoid antagonist of claim 1.

16. A method for reducing or abolishing adverse events in a subject receiving retinoid agonist treatment, which comprises administering to such subject an effective amount of (2E,4E)-(1RS, 2RS)-5-[2-(3,5-di-tert-butyl-2-butoxy-phenyl)-cyclopropyl]-3-methyl-penta-2,4-dienoic acid.

* * * * *